(12) United States Patent
Fastrez et al.

(10) Patent No.: US 7,138,265 B1
(45) Date of Patent: Nov. 21, 2006

(54) CHIMERIC TARGET MOLECULES HAVING A REGULATABLE ACTIVITY

(75) Inventors: Jacques Fastrez, Thorembais-Saint-Trond (BE); Daniel Legendre, La Hulpe (BE); Patrice Soumillion, Grez-Doiceau (BE)

(73) Assignee: Université Catholique de Louvain, Louvain-la-Neuve (BE)

( * ) Notice: Subject to any disclaimer, the term of this patent is extended or adjusted under 35 U.S.C. 154(b) by 0 days.

(21) Appl. No.: 08/978,607

(22) Filed: Nov. 26, 1997

Related U.S. Application Data

(63) Continuation-in-part of application No. 08/757,425, filed on Jan. 31, 1997, now Pat. No. 6,500,660.

(51) Int. Cl.
*C12N 9/86* (2006.01)

(52) U.S. Cl. ..................... 435/231; 435/183

(58) Field of Classification Search ............ 435/237.1, 435/69.1, 69.7, 252.3, 320.1, 662, 183, 7.1, 435/231; 536/23.2, 23.7; 530/300, 350; 424/192.1

See application file for complete search history.

(56) References Cited

OTHER PUBLICATIONS

Rodrigues et al. Cancer Research 55 : 63-70, Jan. 1, 1995.*

* cited by examiner

*Primary Examiner*—Tekchand Saidha
(74) *Attorney, Agent, or Firm*—Finnegan, Henderson, Farabow, Garrett and Dunner, LLP

(57) ABSTRACT

The present invention relates to a chimeric target molecule having an activity which can be regulated or modulated by a binding molecule. The invention also relates to methods of using the chimeric target molecule to detect the presence and/or amount of a desired analyte in a sample. The analyte is a binding molecule, or a competitor of a binding molecule, which binding molecule, upon binding to the target molecule, alters the activity of the target molecule in a detectable way. In one aspect of the invention, a binding molecule binds to the chimeric molecule, inactivating it. An analyte in a test sample competes and/or displaces the binding molecule from the chimera, reactivating it. The reappearance of activity in the presence of the analyte indicates its existence in the test sample existence and amount. Another aspect of the invention relates to a binding molecule which regulates a chimeric target molecule and methods of producing it.

8 Claims, 8 Drawing Sheets

```
      ApaII                                                       XhoI
    GTGCACAGCCAGAAACGCTGGTGAAAGTAAAAGATGCTGAAGATCAGTTGGGTGCTCGAGTGGGTTACATCGA
       Q  P  E  T  L  V  K  V  K  D  A  E  D  Q  L  G  A  R  V  G  Y  I  E
       26                31                        41

ACTGGATCTCAACAGCGGTAAGATCCTTGAGAGTTTTCGCCCCGAAGAACGTTTTCCAATGATGAGCACTTTTAAAGTTC
     L  D  L  N  S  G  K  I  L  E  S  F  R  P  E  E  R  F  P  M  M  S  T  F  K  V
     51                            61                              71

TGCTATGTGGCGCGGTATTATCCCGTGTTGACGCCGGGCAAGAGCAACTCGGTCGCCGCATACACTATTCTCAGAATGAC
     L  L  C  G  A  V  L  S  R  V  D  A  G  Q  E  Q  L  G  R  R  I  H  Y  S  Q  N  D
                81                              91                             101

TTGGTTGAGTACTCACCAGTCACAGAAAAGCATCTTACGGATGGCATGACAGTAAGAGAATTATGCAGTGCTGCCATAAC
     L  V  E  Y  S  P  V  T  E  K  H  L  T  D  G  M  T  V  R  E  L  C  S  A  A  I  T
                            111                            121

PvuI
    CATGAGTGATAACACTGCGGCCAACTTACTTCTGACAACGATCGGAGGACCGAAGGAGCTAACCGCTTTTTTGCACAACA
     M  S  D  N  T  A  A  N  L  L  L  T  T  I  G  G  P  K  E  L  T  A  F  L  H  N
     131                            141                               151

TGGGGGATCATGTAACTCGCCTTGATCGTTGGGAACCGGAGCTGAATGAAGCCATACCAAACGACGAGCGTGACACCACG
     M  G  D  H  V  T  R  L  D  R  W  E  P  E  L  N  E  A  I  P  N  D  E  R  D  T  T
                    161                           171                            181

PstI                 FspI
    ATGCCTGCAGCAATGGCAACAACGTTGCGCAAACTATTAACTGGCGAACTACTTACTCTAGCTTCCCGGCAACAATTAAT
     M  P  A  A  M  A  T  T  L  R  K  L  L  T  G  E  L  L  T  L  A  S  R  Q  Q  L  I
                           191                            201

AGACTGGATGGAGGCGGATAAAGTTGCAGGACCACTTCTGCGCTCGGCCCTTCCGGCTGGCTGGTTTATTGCTGATAAAT
      D  W  M  E  A  D  K  V  A  G  P  L  L  R  S  A  L  P  A  G  W  F  I  A  D  K
      211                             221                           231

CTGGAGCCGGTGAGCGTGGGTCTCGCGGTATCATTGCAGCACTGGGGCCAGATGGTAAGCCCTCCCGTATCGTAGTTATC
     S  G  A  G  E  R  G  S  R  G  I  I  A  A  L  G  P  D  G  K  P  S  R  I  V  V  I
               241                            251                            261

TACACGACGGGGAGTCAGGCAACTATGGATGAACGAAATAGACAGATCGCTGAGATAGGTGCCTCACTGATTAAGCATTG
     Y  T  T  G  S  Q  A  T  M  D  E  R  N  R  Q  I  A  E  I  G  A  S  L  I  K  H  W
                            271                            281

NotI
    GGGGATTGAGGGGCGTGCGGCCGC
     G  I  E  G  R  A  A
     291
```

FIG. 1B

| lib1 | lib3 | Catalytic site |
|---|---|---|
| 1. V103 | 4. T271 | 6. S70 |
| 2. E104 | 5. M272 | |
| 3. Y105 | | |

[psa19Aj302] = 2,4 10⁻⁹ M        Kd = 5,7 10⁻⁹ M

Clone p19Rb404.

substrate = PenG

| Kcat-E (s-1) | Kcat-Eab (s-1) | [Et] (nM) | kd (nM) |
|---|---|---|---|
| 134,3 | 11 | 2,4 | 50 |

Clone p66Rb330 substrate = Centa

| Kcat-E (s-1) | Kcat-Eab (s-1) | [Et] (nM) | kd (nM) |
|---|---|---|---|
| 32.8 | 56.5 | 6.4 | 360 | substrate = PADAC

| Kcat-E (s-1) | Kcat-Eab (s-1) | [Et] (nM) | kd (nM) |
|---|---|---|---|
| 636.8 | 245 | 0.64 | 360 |

SEQUENCE LISTING

```
<160> NUMBER OF SEQ ID NOS: 78

<210> SEQ ID NO 1
<211> LENGTH: 6
<212> TYPE: PRT
<213> ORGANISM: Artificial Sequence
<220> FEATURE:
<223> OTHER INFORMATION: Mimetope

<400> SEQUENCE: 1

Lys Ala Gly Ser Asp Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Mimetope

<400> SEQUENCE: 2

Gly Gly Pro Arg Ser Trp
1               5

<210> SEQ ID NO 3
<211> LENGTH: 6
<212> TYPE: PRT
<213> ORGANISM: Artificial Sequence
<220> FEATURE:
<223> OTHER INFORMATION: Mimetope

<400> SEQUENCE: 3

Lys Asn Cys Gly Lys Cys
1               5

<210> SEQ ID NO 4
<211> LENGTH: 6
<212> TYPE: PRT
<213> ORGANISM: Artificial Sequence
<220> FEATURE:
<223> OTHER INFORMATION: Mimetope

<400> SEQUENCE: 4

Asp Val Pro Gly Ala Gly
```

```
<210> SEQ ID NO 5
<211> LENGTH: 6
<212> TYPE: PRT
<213> ORGANISM: Artificial Sequence
<220> FEATURE:
<223> OTHER INFORMATION: Mimetope

<400> SEQUENCE: 5

Lys Ser Gly Glu His Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Mimetope

<400> SEQUENCE: 6

Arg Ala Gly Asn His Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Mimetope

<400> SEQUENCE: 7

Asp Pro Pro Gly Tyr Gly
1               5

<210> SEQ ID NO 8
<211> LENGTH: 6
<212> TYPE: PRT
<213> ORGANISM: Artificial Sequence
<220> FEATURE:
<223> OTHER INFORMATION: Mimetope

<400> SEQUENCE: 8

Arg Phe Gly Asn Asp Trp
1               5

<210> SEQ ID NO 9
<211> LENGTH: 4
<212> TYPE: PRT
<213> ORGANISM: Artificial Sequence
<220> FEATURE:
<223> OTHER INFORMATION: Mimetope

<400> SEQUENCE: 9

Arg Ser His Trp
1

<210> SEQ ID NO 10
<211> LENGTH: 6
<212> TYPE: PRT
<213> ORGANISM: Artificial Sequence
<220> FEATURE:
<223> OTHER INFORMATION: Mimetope

<400> SEQUENCE: 10

Asp Gln Met Gly Gly Gly
1               5
```

```
<210> SEQ ID NO 11
<211> LENGTH: 6
<212> TYPE: PRT
<213> ORGANISM: Artificial Sequence
<220> FEATURE:
<223> OTHER INFORMATION: Mimetope

<400> SEQUENCE: 11

Arg Ala Gly Ser Thr Trp
1               5

<210> SEQ ID NO 12
<211> LENGTH: 6
<212> TYPE: PRT
<213> ORGANISM: Artificial Sequence
<220> FEATURE:
<223> OTHER INFORMATION: Mimetope

<400> SEQUENCE: 12

Lys Gly Gly Leu Glu Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Mimetope

<400> SEQUENCE: 13

Leu Pro Asn Leu Asp Thr
1               5

<210> SEQ ID NO 14
<211> LENGTH: 6
<212> TYPE: PRT
<213> ORGANISM: Artificial Sequence
<220> FEATURE:
<223> OTHER INFORMATION: Mimetope

<400> SEQUENCE: 14

Asn Arg Ser Gly Ser Trp
1               5

<210> SEQ ID NO 15
<211> LENGTH: 6
<212> TYPE: PRT
<213> ORGANISM: Artificial Sequence
<220> FEATURE:
<223> OTHER INFORMATION: Mimetope

<400> SEQUENCE: 15

Asp Val Ser Gly Gly His
1               5

<210> SEQ ID NO 16
<211> LENGTH: 6
<212> TYPE: PRT
<213> ORGANISM: Artificial Sequence
<220> FEATURE:
<223> OTHER INFORMATION: Mimetope

<400> SEQUENCE: 16

Leu His Ser Gly Gly Trp
1               5
```

```
<210> SEQ ID NO 17
<211> LENGTH: 6
<212> TYPE: PRT
<213> ORGANISM: Artificial Sequence
<220> FEATURE:
<223> OTHER INFORMATION: Mimetope

<400> SEQUENCE: 17

Ser Arg Ala Gly Gly Tyr
1               5

<210> SEQ ID NO 18
<211> LENGTH: 5
<212> TYPE: PRT
<213> ORGANISM: Artificial Sequence
<220> FEATURE:
<223> OTHER INFORMATION: Mimetope

<400> SEQUENCE: 18

Thr Ala Lys Met Asp
1               5

<210> SEQ ID NO 19
<211> LENGTH: 5
<212> TYPE: PRT
<213> ORGANISM: Artificial Sequence
<220> FEATURE:
<223> OTHER INFORMATION: Mimetope

<400> SEQUENCE: 19

Pro Thr Val Ser Met
1               5

<210> SEQ ID NO 20
<211> LENGTH: 5
<212> TYPE: PRT
<213> ORGANISM: Artificial Sequence
<220> FEATURE:
<223> OTHER INFORMATION: Mimetope

<400> SEQUENCE: 20

Arg Gln Ser Thr Met
1               5

<210> SEQ ID NO 21
<211> LENGTH: 5
<212> TYPE: PRT
<213> ORGANISM: Artificial Sequence
<220> FEATURE:
<223> OTHER INFORMATION: Mimetope

<400> SEQUENCE: 21

Gly Arg Thr Thr Met
1               5

<210> SEQ ID NO 22
<211> LENGTH: 5
<212> TYPE: PRT
<213> ORGANISM: Artificial Sequence
<220> FEATURE:
<223> OTHER INFORMATION: Mimetope

<400> SEQUENCE: 22

Ser Asp Gln Pro Leu
1               5
```

```
<210> SEQ ID NO 23
<211> LENGTH: 5
<212> TYPE: PRT
<213> ORGANISM: Artificial Sequence
<220> FEATURE:
<223> OTHER INFORMATION: Mimetope

<400> SEQUENCE: 23

His Thr Ala Ser Met
1               5

<210> SEQ ID NO 24
<211> LENGTH: 5
<212> TYPE: PRT
<213> ORGANISM: Artificial Sequence
<220> FEATURE:
<223> OTHER INFORMATION: Mimetope

<400> SEQUENCE: 24

Lys Ser Val Gly Leu
1               5

<210> SEQ ID NO 25
<211> LENGTH: 5
<212> TYPE: PRT
<213> ORGANISM: Artificial Sequence
<220> FEATURE:
<223> OTHER INFORMATION: Mimetope

<400> SEQUENCE: 25

Ala Asn Ile Ser Leu
1               5

<210> SEQ ID NO 26
<211> LENGTH: 5
<212> TYPE: PRT
<213> ORGANISM: Artificial Sequence
<220> FEATURE:
<223> OTHER INFORMATION: Mimetope

<400> SEQUENCE: 26

Pro Val Ala Pro Ile
1               5

<210> SEQ ID NO 27
<211> LENGTH: 5
<212> TYPE: PRT
<213> ORGANISM: Artificial Sequence
<220> FEATURE:
<223> OTHER INFORMATION: Mimetope

<400> SEQUENCE: 27

Arg Pro Thr Thr Leu
1               5

<210> SEQ ID NO 28
<211> LENGTH: 5
<212> TYPE: PRT
<213> ORGANISM: Artificial Sequence
<220> FEATURE:
<223> OTHER INFORMATION: Mimetope

<400> SEQUENCE: 28

Pro Asn Ala Asn Met
1               5

<210> SEQ ID NO 29
```

```
<211> LENGTH: 6
<212> TYPE: PRT
<213> ORGANISM: Artificial Sequence
<220> FEATURE:
<223> OTHER INFORMATION: Mimetope

<400> SEQUENCE: 29

Ala Thr Ser Phe Ala Pro
1               5

<210> SEQ ID NO 30
<211> LENGTH: 6
<212> TYPE: PRT
<213> ORGANISM: Artificial Sequence
<220> FEATURE:
<223> OTHER INFORMATION: Mimetope

<400> SEQUENCE: 30

Arg Arg Lys Gln Pro Thr
1               5

<210> SEQ ID NO 31
<211> LENGTH: 6
<212> TYPE: PRT
<213> ORGANISM: Artificial Sequence
<220> FEATURE:
<223> OTHER INFORMATION: Mimetope

<400> SEQUENCE: 31

Thr Ala His Val Ala Ser
1               5

<210> SEQ ID NO 32
<211> LENGTH: 6
<212> TYPE: PRT
<213> ORGANISM: Artificial Sequence
<220> FEATURE:
<223> OTHER INFORMATION: Mimetope

<400> SEQUENCE: 32

Thr Asn Lys Gln Pro Ser
1               5

<210> SEQ ID NO 33
<211> LENGTH: 6
<212> TYPE: PRT
<213> ORGANISM: Artificial Sequence
<220> FEATURE:
<223> OTHER INFORMATION: Mimetope

<400> SEQUENCE: 33

Lys Ser Tyr Thr Pro Glu
1               5

<210> SEQ ID NO 34
<211> LENGTH: 6
<212> TYPE: PRT
<213> ORGANISM: Artificial Sequence
<220> FEATURE:
<223> OTHER INFORMATION: Mimetope

<400> SEQUENCE: 34

Lys Trp Asn Tyr Thr Thr
1               5

<210> SEQ ID NO 35
<211> LENGTH: 6
```

```
<212> TYPE: PRT
<213> ORGANISM: Artificial Sequence
<220> FEATURE:
<223> OTHER INFORMATION: Mimetope

<400> SEQUENCE: 35

Gly Glu His Glu Ala Gly
1               5

<210> SEQ ID NO 36
<211> LENGTH: 6
<212> TYPE: PRT
<213> ORGANISM: Artificial Sequence
<220> FEATURE:
<223> OTHER INFORMATION: Mimetope

<400> SEQUENCE: 36

Glu Glu Asn Gly Arg Pro
1               5

<210> SEQ ID NO 37
<211> LENGTH: 6
<212> TYPE: PRT
<213> ORGANISM: Artificial Sequence
<220> FEATURE:
<223> OTHER INFORMATION: Mimetope

<400> SEQUENCE: 37

Gln Leu Gln Val Pro Pro
1               5

<210> SEQ ID NO 38
<211> LENGTH: 6
<212> TYPE: PRT
<213> ORGANISM: Artificial Sequence
<220> FEATURE:
<223> OTHER INFORMATION: Mimetope

<400> SEQUENCE: 38

Ala Pro Gly Asn Asp Gly
1               5

<210> SEQ ID NO 39
<211> LENGTH: 6
<212> TYPE: PRT
<213> ORGANISM: Artificial Sequence
<220> FEATURE:
<223> OTHER INFORMATION: Mimetope

<400> SEQUENCE: 39

Ala Gly Ala Thr Tyr Glu
1               5

<210> SEQ ID NO 40
<211> LENGTH: 4
<212> TYPE: PRT
<213> ORGANISM: Artificial Sequence
<220> FEATURE:
<223> OTHER INFORMATION: Mimetope

<400> SEQUENCE: 40

Met Asp Glu Arg
1

<210> SEQ ID NO 41
<211> LENGTH: 6
<212> TYPE: PRT
```

```
<213> ORGANISM: Artificial Sequence
<220> FEATURE:
<223> OTHER INFORMATION: Mimetope

<400> SEQUENCE: 41

Glu Arg Ser Gly His Trp
1               5

<210> SEQ ID NO 42
<211> LENGTH: 5
<212> TYPE: PRT
<213> ORGANISM: Artificial Sequence
<220> FEATURE:
<223> OTHER INFORMATION: Mimetope

<400> SEQUENCE: 42

Leu Ala Ser Gly Tyr
1               5

<210> SEQ ID NO 43
<211> LENGTH: 6
<212> TYPE: PRT
<213> ORGANISM: Artificial Sequence
<220> FEATURE:
<223> OTHER INFORMATION: Mimetope

<400> SEQUENCE: 43

Val Arg Ser Gly Pro Trp
1               5

<210> SEQ ID NO 44
<211> LENGTH: 6
<212> TYPE: PRT
<213> ORGANISM: Artificial Sequence
<220> FEATURE:
<223> OTHER INFORMATION: Mimetope

<400> SEQUENCE: 44

Arg Thr Ala Lys Val Ser
1               5

<210> SEQ ID NO 45
<211> LENGTH: 6
<212> TYPE: PRT
<213> ORGANISM: Artificial Sequence
<220> FEATURE:
<223> OTHER INFORMATION: Mimetope

<400> SEQUENCE: 45

Gln Lys Val Glu Pro Ser
1               5

<210> SEQ ID NO 46
<211> LENGTH: 6
<212> TYPE: PRT
<213> ORGANISM: Artificial Sequence
<220> FEATURE:
<223> OTHER INFORMATION: Mimetope

<400> SEQUENCE: 46

Thr Gly Val Tyr Pro Ser
1               5

<210> SEQ ID NO 47
<211> LENGTH: 6
<212> TYPE: PRT
<213> ORGANISM: Artificial Sequence
```

```
<220> FEATURE:
<223> OTHER INFORMATION: Mimetope

<400> SEQUENCE: 47

Gln Gly Pro Trp Ala Ser
1               5

<210> SEQ ID NO 48
<211> LENGTH: 6
<212> TYPE: PRT
<213> ORGANISM: Artificial Sequence
<220> FEATURE:
<223> OTHER INFORMATION: Mimetope

<400> SEQUENCE: 48

Ile Gly Asp Tyr Ser Lys
1               5

<210> SEQ ID NO 49
<211> LENGTH: 6
<212> TYPE: PRT
<213> ORGANISM: Artificial Sequence
<220> FEATURE:
<223> OTHER INFORMATION: Mimetope

<400> SEQUENCE: 49

Thr Gly Asn Gln Ala Thr
1               5

<210> SEQ ID NO 50
<211> LENGTH: 6
<212> TYPE: PRT
<213> ORGANISM: Artificial Sequence
<220> FEATURE:
<223> OTHER INFORMATION: Mimetope

<400> SEQUENCE: 50

Ser Asn Gly Glu His Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Mimetope

<400> SEQUENCE: 51

Ser Gly His Glu Pro Thr
1               5

<210> SEQ ID NO 52
<211> LENGTH: 6
<212> TYPE: PRT
<213> ORGANISM: Artificial Sequence
<220> FEATURE:
<223> OTHER INFORMATION: Mimetope

<400> SEQUENCE: 52

Asp Ser Lys Glu Thr Ser
1               5

<210> SEQ ID NO 53
<211> LENGTH: 6
<212> TYPE: PRT
<213> ORGANISM: Artificial Sequence
<220> FEATURE:
```

<223> OTHER INFORMATION: Mimetope

<400> SEQUENCE: 53

Thr Ala Arg Trp Ala Asn
1               5

<210> SEQ ID NO 54
<211> LENGTH: 6
<212> TYPE: PRT
<213> ORGANISM: Artificial Sequence
<220> FEATURE:
<223> OTHER INFORMATION: Mimetope

<400> SEQUENCE: 54

Thr Ala Asn Glu His Thr
1               5

<210> SEQ ID NO 55
<211> LENGTH: 6
<212> TYPE: PRT
<213> ORGANISM: Artificial Sequence
<220> FEATURE:
<223> OTHER INFORMATION: Mimetope

<400> SEQUENCE: 55

Val Lys Ser Gly Val Ala
1               5

<210> SEQ ID NO 56
<211> LENGTH: 7
<212> TYPE: PRT
<213> ORGANISM: Artificial Sequence
<220> FEATURE:
<223> OTHER INFORMATION: Mimetope

<400> SEQUENCE: 56

Val Lys Ser Gly Asn Thr Trp
1               5

<210> SEQ ID NO 57
<211> LENGTH: 7
<212> TYPE: PRT
<213> ORGANISM: Artificial Sequence
<220> FEATURE:
<223> OTHER INFORMATION: Mimetope

<400> SEQUENCE: 57

Val Asp Arg Thr Lys Gly Trp
1               5

<210> SEQ ID NO 58
<211> LENGTH: 7
<212> TYPE: PRT
<213> ORGANISM: Artificial Sequence
<220> FEATURE:
<223> OTHER INFORMATION: Mimetope

<400> SEQUENCE: 58

Val Asp Gly Pro Asn Gly His
1               5

<210> SEQ ID NO 59
<211> LENGTH: 7
<212> TYPE: PRT
<213> ORGANISM: Artificial Sequence
<220> FEATURE:
<223> OTHER INFORMATION: Mimetope

```
<400> SEQUENCE: 59

His Pro Gln Asn Asp Asp Met
1               5

<210> SEQ ID NO 60
<211> LENGTH: 7
<212> TYPE: PRT
<213> ORGANISM: Artificial Sequence
<220> FEATURE:
<223> OTHER INFORMATION: Mimetope

<400> SEQUENCE: 60

His Pro Gln Asn Asp Asp Met
1               5

<210> SEQ ID NO 61
<211> LENGTH: 7
<212> TYPE: PRT
<213> ORGANISM: Artificial Sequence
<220> FEATURE:
<223> OTHER INFORMATION: Mimetope

<400> SEQUENCE: 61

His Pro Gln Asn Asp Asp Met
1               5

<210> SEQ ID NO 62
<211> LENGTH: 7
<212> TYPE: PRT
<213> ORGANISM: Artificial Sequence
<220> FEATURE:
<223> OTHER INFORMATION: Mimetope

<400> SEQUENCE: 62

His Pro Gln Gly Asp Asn Met
1               5

<210> SEQ ID NO 63
<211> LENGTH: 7
<212> TYPE: PRT
<213> ORGANISM: Artificial Sequence
<220> FEATURE:
<223> OTHER INFORMATION: Mimetope

<400> SEQUENCE: 63

His Pro Gln Gly Asp Ser Met
1               5

<210> SEQ ID NO 64
<211> LENGTH: 7
<212> TYPE: PRT
<213> ORGANISM: Artificial Sequence
<220> FEATURE:
<223> OTHER INFORMATION: Mimetope

<400> SEQUENCE: 64

His Pro Gln Asn Asp Asp Met
1               5

<210> SEQ ID NO 65
<211> LENGTH: 7
<212> TYPE: PRT
<213> ORGANISM: Artificial Sequence
<220> FEATURE:
<223> OTHER INFORMATION: Mimetope
```

```
<400> SEQUENCE: 65

Ser Asp Gly His Arg Leu Met
1               5

<210> SEQ ID NO 66
<211> LENGTH: 7
<212> TYPE: PRT
<213> ORGANISM: Artificial Sequence
<220> FEATURE:
<223> OTHER INFORMATION: Mimetope

<400> SEQUENCE: 66

Ser Asp Gly His Arg Leu Met
1               5

<210> SEQ ID NO 67
<211> LENGTH: 7
<212> TYPE: PRT
<213> ORGANISM: Artificial Sequence
<220> FEATURE:
<223> OTHER INFORMATION: Mimetope

<400> SEQUENCE: 67

Ser Asp Gly His Arg Leu Met
1               5

<210> SEQ ID NO 68
<211> LENGTH: 7
<212> TYPE: PRT
<213> ORGANISM: Artificial Sequence
<220> FEATURE:
<223> OTHER INFORMATION: Mimetope

<400> SEQUENCE: 68

Ser Asp Gly His Arg Leu Met
1               5

<210> SEQ ID NO 69
<211> LENGTH: 7
<212> TYPE: PRT
<213> ORGANISM: Artificial Sequence
<220> FEATURE:
<223> OTHER INFORMATION: Mimetope

<400> SEQUENCE: 69

Ser Asp Gly His Arg Leu Met
1               5

<210> SEQ ID NO 70
<211> LENGTH: 7
<212> TYPE: PRT
<213> ORGANISM: Artificial Sequence
<220> FEATURE:
<223> OTHER INFORMATION: Mimetope

<400> SEQUENCE: 70

Val Lys Gly Gly His Gly Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Mimetope

<400> SEQUENCE: 71
```

Thr Pro Gly Ser Leu Gln Met
1               5

<210> SEQ ID NO 72
<211> LENGTH: 7
<212> TYPE: PRT
<213> ORGANISM: Artificial Sequence
<220> FEATURE:
<223> OTHER INFORMATION: Mimetope

<400> SEQUENCE: 72

Ser Ala His Gln Asp Tyr Ile
1               5

<210> SEQ ID NO 73
<211> LENGTH: 7
<212> TYPE: PRT
<213> ORGANISM: Artificial Sequence
<220> FEATURE:
<223> OTHER INFORMATION: Mimetope

<400> SEQUENCE: 73

Thr Pro Gly Ser Leu Gln Met
1               5

<210> SEQ ID NO 74
<211> LENGTH: 7
<212> TYPE: PRT
<213> ORGANISM: Artificial Sequence
<220> FEATURE:
<223> OTHER INFORMATION: Mimetope

<400> SEQUENCE: 74

Thr Pro Gly Ser Leu Gln Met
1               5

<210> SEQ ID NO 75
<211> LENGTH: 7
<212> TYPE: PRT
<213> ORGANISM: Artificial Sequence
<220> FEATURE:
<223> OTHER INFORMATION: Mimetope

<400> SEQUENCE: 75

Thr Pro Gly Ser Leu Gln Met
1               5

<210> SEQ ID NO 76
<211> LENGTH: 7
<212> TYPE: PRT
<213> ORGANISM: Artificial Sequence
<220> FEATURE:
<223> OTHER INFORMATION: Mimetope

<400> SEQUENCE: 76

Asp Gly Ser Arg Ile Gln Met
1               5

<210> SEQ ID NO 77
<211> LENGTH: 7
<212> TYPE: PRT
<213> ORGANISM: Artificial Sequence
<220> FEATURE:
<223> OTHER INFORMATION: Mimetope

<400> SEQUENCE: 77

```
Asp Gly Ser Arg Ile Gln Met
1               5

<210> SEQ ID NO 78
<211> LENGTH: 7
<212> TYPE: PRT
<213> ORGANISM: Artificial Sequence
<220> FEATURE:
<223> OTHER INFORMATION: Mimetope

<400> SEQUENCE: 78

Asp Gly Ser Arg Ile Gln Met
1               5
```

CHIMERIC TARGET MOLECULES HAVING A REGULATABLE ACTIVITY

CROSS-REFERENCE TO RELATED APPLICATION

This application is a continuation-in-part application of application Ser. No. 08/757,425, filed Jan. 31, 1997 now U.S. Pat. No. 6,500,660.

BACKGROUND OF THE INVENTION

The development of assays for measuring the presence and amount of desired substances is highly desirable for a variety of purposes, including for medical, veterinary, research, and environmental uses. It is further desirable to design and isolate molecules having an activity which is regulatable by a desired substance. These regulatable molecules are useful to detect the amount and presence of a desired analyte, utilizing the ability of the analyte to directly or indirectly (e.g., by competition) regulate the molecule's activity.

DESCRIPTION OF THE INVENTION

The present invention relates to a chimeric target molecule having an activity which can be regulated or modulated by a binding molecule. The invention also relates to methods of using the chimeric target molecule to detect the presence and/or amount of a desired analyte in a sample. The analyte is a binding molecule, or a ligand of a binding molecule, which binding molecule, upon binding to the target molecule, alters the activity of the target molecule in a detectable way. In one aspect of the invention, a binding molecule binds to the chimeric molecule, inactivating it. An analyte in a test sample competes and/or displaces the binding molecule from the chimera, reactivating it. The reappearance of activity in the presence of the analyte indicates its existence and amount in the test sample. Another aspect of the invention relates to a binding molecule which regulates a chimeric target molecule and methods of producing it.

In accordance with the present invention, a desired target molecule (TM) can be modified to have at least one binding site moiety (BSM) to which a binding molecule (BM) can attach. Upon attachment of the BM to the BSM, an activity associated with the TM is altered in a detectable way, e.g., increasing or reducing the activity of the TM. Thus, the BSM can act as a regulatory switch, turning on or off (all or in part) an activity of a desired TM in response to the binding of a BM. The BSM can also be selected so that binding of the binding molecule regulates the activation of the target molecule. In accordance with the present invention, a mimotope is the preferred BSM. A BSM can be engineered into a target molecule by the insertion of sequences, by the replacement of sequences present in the molecule with new sequences, by mutagenesis of sequences already present in the molecule, etc. Engineering can be accomplished according to methods available to the skilled worker.

The term "chimeric" target molecule, e.g., a "chimeric enzyme," means the resultant product after the binding site moiety has been inserted into the target molecule or after a portion of the target molecule has been replaced by the binding site moiety. For clarity, before engineering of the BSM, the target molecule is referred to as the starting target molecule. Thus, if an enzyme is the starting material, it is referred to as the "starting enzyme." After engineering of the BSM, the starting enzyme is identified as a "chimeric enzyme." In the examples below, β-lactamase is used as a starting enzyme into which a binding site moiety comprising amino acids, is engineered to produce a chimeric enzyme. It is chimeric because it is comprised of amino acids of the starting enzyme and amino acids of a binding site moiety.

The term "binding molecule" means a molecule that specifically binds or attaches to a binding site moiety. By the term "specific," it is meant that the binding molecule recognizes the defined sequence of amino acids within or including the amino acid sequence of the binding site moiety. Specificity can be a function of the linear amino acid sequence of the binding site moiety, alone, or in combination with amino acids originally present in the target molecule or at an insertion or replacement at another site. Various binding molecules can be employed, including antibodies, polypeptides, aptamers, nucleic acids, drugs, and chemical ligands. Antibodies can be monoclonal, poly-clonal, single-chain, genetically-engineered antibodies, etc., as known in the art. See, e.g., Reiter et al., *Nature Biotechnology*, 14:1239–1245, 1996; Bird et al., *Science*, 242:423–426, 1988.

A binding molecule can bind to a specific portion of a macromolecule called an epitope or a determinant. The epitope can be a linear determinant or a conformational determinant. See, e.g., Abbas et al., *Cellular and Molecular Immunology*, Second Edition, W.B. Saunders Co., 1991, especially, pages 47–49. A "mimotope" is a determinant which is recognized by the same binding molecule as a particular "epitope" but which has a different composition from the "epitope." For example, a binding molecule can be an antibody which recognizes (i.e., binds to) an epitope comprising a linear sequence of amino acids. A "mimotope" of this epitope comprises a different linear sequence of amino acids but which is still recognized by the same antibody. The "mimotope" differs by at least one amino acid from the "epitope." A mimotope can mime a hapten and other molecules, including non-proteinaceous molecules or moieties, e.g., carbohydrate, biotin, etc. As mentioned, the mimotope can also be a conformational determinant formed by amino acid residues or other constituents from separated portions of the chimeric molecule. Further, the mimotope can comprise constituents (e.g., amino acids) already present in the starting TM and which remained (i.e., were not replaced) in the chimeric TM. A mimotope can be selected as discussed below, e.g., in the examples, by engineering random amino acids into a target and screening or selecting for recognition by a desired binding molecule.

An advantage of employing a mimotope is that no knowledge of the structure of the epitope is required. This knowledge is in general difficult to acquire, particularly if the epitope is non-linear. In one aspect of the invention, a library of mimotopes is created and engineered, e.g., inserted, into a target molecule, preferably into a loop. The resultant chimeric molecule is then screened or selected for retention of activity. The mimotope can be extracted from a random sequence, e.g., containing five amino acids, preferably six amino acids (a random hexapeptide), or seven, eight, nine, ten, amino acids in length. In this aspect of the invention, upon identification of chimeric target molecules which have retained activity, they are then screened for recognition by the desired binding molecule. The binding molecule can be an antibody to a carbohydrate or other non-proteinaceous hapten or non-hapten, or an amino acid sequence. In especially the latter case, no sequence information is required to implement the invention.

The target molecule can be selected for a desired detectable activity. For example, the TM can be: β-lactamase: P. Soumillion et al., *J. Mol. Biol.*, 237:415–422, 1994; Plasmin: L. Jespers et al., conference communication; Prostate specific antigen: R. Eerola et al., *Biochem. Biophys. Res. Comm.*, 200:1346–1352, 1994; Subtilisin: P. Soumillion et al., *Appl. Biochem. Biotechnol.*, 47:175–190, 1994; Trypsin: D. R. Corey et al., *Gene*, 128:129–134, 1993; Alkaline phosphatase: J. McCafferty et al., *Prot. Enging.*, 4:955–961; β-galactosidase: I. N. Maruyama et al., *Proc. Natl. Acad. Sci. USA*, 91:8273–8277, 1994; Staphylococcal nuclease: J. Ku & P. G. Schultz, *Bioorg. Med. Chem.*, 2:1413–5, 1994; and J. Light & R. A. Lerner, *Bioorg. Med. Chem.*, 3:955–67, 1995; Glutathione transferase: M. Widersten & B. Mannervick, *J. Mol. Biol.*, 250:115–122, 1995; Lysozyme: K. Maenaka et al., *Biochem. Biophys. Res. Comm.*, 218:682–687, 1996; and Catalytic antibodies: K. D. Janda et al., *Proc. Natl. Acad. Sci USA*, 91:2532–2536, 1994.

The above-mentioned target molecules have been displayed on phage. They are directly amenable to the method of selection of a BSM. Other enzymes can also be displayed on phage and are useful for the present invention, e.g., esterases, pyruvate kinase, glucose oxidase, lactate dehydrogenase, glucose-6-phosphate dehydrogenase, luciferase. The TM can also be a protein possessing a fluorescent activity (e.g., green fluorescent protein, GFP: Chalfie et al., 1994, *Science*, 263:802; Cheng et al., 1996, *Nature Biotechnology*, 14:606; Levy et al., 1996, *Nature Biotechnology*, 14:610) which is modulated by binding of a BM to a BSM contained within the fluorescent protein. The TM can also be a regulatory molecule which activates/inactivates a second molecule having a detectable activity. For instance, a GTPase activating protein (GAP) stimulates a G-protein, such as ras. The ability of a GAP to activate a G-protein can be modulated by engineering a BSM into the GAP. Upon attachment of a BM to the BSM of a modified GAP, the stimulating activity of the GAP can be modulated. Its upstream effect on G-proteins can be monitored, e.g., by measuring a GTPase activity of the G-protein. See, e.g., Trahey and McCormick, *Science*, 238:542–545, 1987. The TM can also be a subunit of another protein which itself possesses enzymatic or another detectable activity. Additionally, the TM can be a nucleic acid enzyme, e.g., a ribozyme, a hammerhead enzyme, RNAse P, or a hairpin enzyme. If a nucleic acid is used as the target molecule, the engineered binding site moiety would usually comprise nucleotides, either modified or naturally-occurring. The TM can also be a transcription activator or repressor involved in vitro transcription and translation systems; detection of activity can be accomplished at the level of the activity of the expressed enzyme or fluorescent molecule.

Binding of the BM to the chimeric molecule, preferably at the BSM, can affect activity in various ways. The binding molecule can inactivate the chimeric TM. By the term "inactivate", it is meant that the activity of the chimeric TM is reduced or weakened. The binding molecule can inactivate the chimeric TM completely so that it possesses no, or only negligible, activity, or it can inactivate only part of its activity, e.g., Kcat is reduced or Km is increased. A chimeric TM can exist in at least two conformations, an active and inactive conformation. At equilibrium, a population of chimeric TMs will contain a mixture of molecules, some in the active and some in the inactive conformation of a TM. A BM can be selected that binds to an inactive conformation of a TM. When added to the chimeric TM population, attachment of the BM to the inactive TMs can shift the equilibrium of the mixture to the inactive conformation. As a consequence, the mixture will have less activity in the presence of the BM than in its absence. Thus, the binding molecule modulates the activity of the chimeric TM by shifting the population of chimeric TMs to an inactive conformation, thereby reducing the population's activity as a whole. A selected starting enzyme can be serine protease that can exist in two different conformations: an active and an inactive one. The inactive conformation is similar to that of the corresponding zymogen. The equilibrium can be shifted from the active into the inactive conformation by disrupting a salt bridge maintaining the enzyme in its active conformation; this can be done by a pH increase leading to deprotonation of the amino terminal of the peptide chain involved in the salt bridge or by chemical modification of this amino terminal. The energetics of the salt bridge are such that the active conformation is not strongly stabilized (2.9 Kcal/mol, see: A. R. Fersht, *J. Mol. Biol.*, 64:497–509, 1972) so that the equilibrium can be relatively easily shifted to the inactive form. Binding of a BM, e.g., a monoclonal antibody, to the amino acid terminal can shift the equilibrium by several orders of magnitude.

The activation of a chimeric molecule can also be regulated by a BM. The simplest example of activation is the proteolytic cleavage of a peptide bond in a zymogen to transform it into an enzyme. A classical example is the activation of a serine protease, or more specifically the activation of chymotrypsinogen into chymotrypsin by proteolytic cleavage of the peptide bond Arg15-Ile16 by trypsin. An antibody, or other BM, binding to an epitope or a mimotope engineered in the region of the cleaved peptide bond can inhibit the activation. Another example is the inhibition of the phosphorylation or dephosphorylation of an enzyme whose activity is regulated by its state of phosphorylation. Glycogen phosphorylase is an example: when it is phosphorylated on Ser14, it is essentially in its active form, dephosphorylation deactivates the enzyme. Binding of an antibody, or other BM, to a engineered epitope or mimotope in the vicinity of the phosphorylation site would interfere with the activation/deactivation mechanism by phosphorylase kinase and phosphoprotein phosphatase, respectively.

More generally any post-translation modification of an enzyme, that contributes to modulate its activity, can be interfered with by binding a foreign molecule to a BSM (e.g., an antibody).

The binding site moiety can be engineered into any desired position in the target molecule, including as a fusion with the N- and C-termini. One or more, e.g., 2, 3, 4, or 5, BSMs can be engineered into the target moiety at adjacent or different regions. Multiple engineering, e.g., insertions or replacements, to the target molecule can be made for a variety of reasons, e.g., to contribute to the mimotope (e.g., the mimotope can be comprised of amino acids contributed by engineering at two different sites in the target molecule), to provide more than one site to which a binding molecule can bind, to provide one site at which a BM activates the enzyme and another site at which a second BM inactivates an enzyme, etc. An advantage of inserting or replacing amino acid sequences with a mimotope at two sites (or more) is that a discontinuous mimotope can be constructed, providing for high affinity sites to which a binding molecule can attach. Preferably, as discussed above, the resultant chimeric TM retains at least some of its activity after engineering of the BSM. In addition, attachment of a BM to the BSM results in regulating the aforementioned activity of the chimeric target molecule. The latter two aspects, retention of an activity and regulation of the retained activity of the resultant chimeric molecule by a binding molecule, are preferred aspects of the invention. Thus, a preferred site of engineering, e.g., insertion, is a position where the activity of the TM is not eliminated but which, when replaced or modified by the addition of amino acid residues, can act as a regulatory switch for TM activity.

The site where a BSM is engineered, e.g., inserted into and/or replaced, in the TM can be selected by various ways as the skilled worker would know. For example, if the three-dimensional (3D) structure of the TM is known, a site can be selected by specifically identifying a desired location on the molecule to engineer. For some purposes, it may be desirable to select an exposed site on the surface of the target molecule, where the site is available for attachment by the binding molecule. 3D-structure can be determined according to empirical means, e.g., by crystallography, and/or, it can be deduced from known structures and amino acid sequence data. See, e.g., Holm and Sander, *Science*, 273:595–602, 1995. If the 3D-structure is not known, the site of engineering can be selected on the basis of other information, e.g., when the structure of the protein is not known, sites susceptible to limited proteolysis or sites strongly predicted to be loops by secondary structure prediction or by analysis of hydrophobic patterns are suitable for engineering, e.g., insertion or replacement. Alternatively, a BSM can be engineered at random positions within the TM.

The engineered site is preferably not at the active site, more preferably it is at a location remote from it, e.g., about 1, 5, 15, 20, or 25 Å from it. The activity of the chimeric molecule must be regulatable by binding to the inserted or replaced sequence, irrespective of whether the modification is close or remote from the active site.

Target and chimeric molecules can be prepared by methods which are available in the art. For example, genetic engineering can be employed to prepare target and chimeric molecules which comprise amino acid or nucleotide residues. In one embodiment, a cloned gene is employed as the starting material for the starting target molecule and resultant chimeric target molecule. In the examples described below, the cloned gene for the starting enzyme β-lactamase serves as the beginning material to produce the chimeric enzyme. The BSM can be engineered into the starting TM using the various methods available to the skilled worker, e.g., Kunkel, *Proc. Natl. Acad. Sci.,* 82:488–492, 1985; Sayers and Eckstein in "Directed Mutagenesis: A practical approach," McPherson, Ed. IRL Press 1991, pp. 49–69; Munir et al., *J. Biol. Chem.,* 267:6584–6589, 1992; Brennan et al., *Proc. Natl. Acad. Sci.,* 92:5783–5787, 1995. Engineering can also be accomplished using a replacement vector via homologous recombination. For the purposes of the present invention, when a sequence within a starting gene has been mutagenized to the extent that the amino acid sequence differs from the starting sequence, the polypeptide coded for the resultant gene is chimeric. It is chimeric since a different amino acid sequence, i.e., a binding site moiety, has been engineered into the starting target molecule. In the specific example where the starting material is an enzyme, and the enzyme is mutagenized by changing its nucleotide sequence, a resultant chimeric enzyme will comprise an amino acid binding site moiety which has replaced the naturally-occurring amino acid sequences. In one embodiment, the sequence of the gene encoding a wild type enzyme (or other polypeptide) is modified by the site directed mutagenesis according to the Kunkel or Eckstein protocols to introduce two restriction sites upstream and downstream from the region of the gene targeted for engineering; preferentially, a mutation is introduced in the coding sequence at the same time so that the encoded enzyme is inactive; the plasmid, phagemid or phage containing the modified gene will be called the "vector." This vector is digested at the new restriction sites with the corresponding restriction enzymes and the small fragment encoding the sequence between the sites is discarded. In parallel, synthetic degenerate oligonucleotide libraries are prepared according to the method of Munir et al., *J. Biol. Chem.,* 267:6584–6589, 1992; they contain, in between the adequate restriction sites, degenerate nucleotide sequences encoding random replacements of the corresponding residues in the protein sequence. Alternatively, the wild type sequence is replaced by a longer nucleotide sequence that will encode the insertion of a random polypeptide in the corresponding position in the protein sequence. After restriction, the synthetic oligonucleotides are ligated with the purified large fragment of the digested vector and the ligation mixture is used to transform *E. coli* cells. Typically, libraries containing about $10^6$ and $10^8$ transformants are produced. Clones producing active enzymes are selected from these (see below). Recombination of clones producing active enzymes in two libraries where random mutations are introduced in different parts of the sequence is done to produce enzymes with discontinuous mimotopes.

In one embodiment where genetic engineering is utilized, a gene coding for a target molecule, e.g., an enzyme, can be cloned into an expression vector suited for expression of a polypeptide in a desired host. Various hosts are contemplated, including, mammalian cells (e.g., human, monkey, or rodent, such as HeLa, COS, Ltk-, or CHO), insect cells (e.g., Sf9 or *Drosophila*), bacteria (e.g., *E. coli, Streptococcus*, or *bacillus*), yeast, fungi, or plants. See, also *Methods in Enzymology*, Volume 185, ed., D. V. Goeddel. Sf9 expression can be accomplished in analogy to Graziani et al., *Oncogene,* 7:229–235, 1992. Filamentous phage systems have been used to express and select peptides in bacteria that attach to binding molecules, including antibodies (Scott and Smith, 249:386–390, 1990; Grihalde et al., *Gene,* 166: 185–195, 1995), streptavidin (Kay et al., *Gene,* 128:59–65, 1993; Devlin et al., *Science,* 249:404–406, 1990), ribonuclease DNA (Rebor and Pabo, *Science,* 263:671–673, 1994). See, also, Jespers et al., *Biotechnology,* 13:378–382, 1995. See, also, Parmley and Smith, *Gene,* 76:305–318, 1985; de la Cruz et al., *J. Biol. Chem.,* 263:4318–4322, 1988; Bass et al., *Proteins,* 8:309–314, 1990; Cwirla et al., *Proc. Natl. Acad. Sci. USA,* 87:6378–6382, 1990; McCafferty et al., *Nature,* 348:552–554, 1990; Clackson et al., *Nature,* 352: 624–628, 1991; Lowman et al., *Biochemistry,* 30:10823–10838, 1991; J. McCafferty et al., *Prot. Eng., pp.* 955–961, 1991; Kang et al., *Proc. Natl. Acad. Sci. USA,* 88:4363–4366, 1991; Barbas et al., *Proc. Natl. Acad. Sci. USA,* 88:7978–7982, 1991; Roberts et al., *Proc. Natl. Acad. Sci. USA,* 89:2429–2433, 1992. Preferred polypeptides for filamentous phage expression systems are those which are properly folded on the phage, or at least, displayed on the phage in a fully active form. To identify whether a desired starting molecule is suitable, a nucleic acid coding for the molecule is cloned into the phage in a manner suitable for expression. The expressed molecule is then assayed for an activity in accordance with conventional methods. Engineering of a BSM into the starting molecule can then be accomplished in accordance with the above-mentioned procedures. See, e.g., Grihalde et al. Expression control sequences are selected for host compatibility and a desired purpose, e.g., high copy number, high amounts, induction, amplification, controlled expression, etc. Other sequences which can be employed, include enhancers such as from SV40, CMV, inducible promoters, or other elements which allow selective or specific cell expression.

The invention also relates to nucleic acids which code for a chimeric target molecule. Such a nucleic acid can further comprise various sequences, e.g., an expression control sequence(s) operably linked to a nucleotide sequence coding for the chimeric target molecule. The phrase "expression control sequence" means a nucleic acid sequence which regulates expression of a nucleic acid to which it is operably linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. A nucleic acid coding for a chimeric molecule also includes nucleic acids which hybridize to it, e.g., under stringent conditions, such as conditions that allow the selection of at least 95% to 99% nucleotide identity. For a chimeric TM which is a polypeptide, a nucleic acid coding for it includes, e.g., nucleotide degeneracy. Nucleic acids include DNA and RNA.

Chemical and/or synthetic methods can also be used to create the chimeric molecule, e.g., the methods of building compounds by combinatorial chemistry, as the skilled worker would know.

As mentioned above, an aspect of the present invention involves chimeric target molecules which have an activity that can be regulated or modulated by a binding molecule. By the phrase "whereby the activity of the chimeric target molecule is modulated upon binding of a binding molecule," it is meant that attachment of the binding molecule to the chimeric TM, preferably at the BSM, affects the activity of the chimeric TM in a detectable way. If the chimeric TM is an enzyme such as β-lactamase, the binding molecule will affect its activity in hydrolyzing the β-lactam bond. The effect of the binding molecule can be to reduce or even eliminate the activity, e.g., reduce or eliminate its ability to cleave the β-lactam bond. The binding molecule can also affect activity in other ways, e.g, increase it, change its specificity, activate it; etc.

In one preferred embodiment, random peptide sequences are engineered at a selected site on a target molecule, e.g., an enzyme. After modification of the starting target molecule to produce a library containing the resultant chimeric target molecule with a BSM engineered by insertion or replacement, it is desirable to select those chimeric molecules which have retained an activity of the starting target molecule. By the phrase, "the chimeric target molecule has an activity of the starting target molecule," it is meant that the starting TM has an activity and the resultant chimeric TM has an activity, as well. The activity of the chimeric TM can be different quantitatively or qualitatively from the starting TM. By way of illustration, in the examples below, the starting enzyme is β-lactamase. β-lactamase is an enzyme which hydrolyzes a β-lactam bond. Various compounds can be used as substrates, including penicillins, cephalosporins, ampicillin, etc. A chimeric β-lactamase having a binding site moiety, either replacing or inserted in addition to naturally-occurring amino acids, will possess the ability to hydrolyse a β-lactam bond. This activity in the chimeric β-lactamase can be, e.g., greater or less than the starting enzyme (e.g., having a different Kcat or a different Km), and/or have a different substrate specificity.

The first step is to select resultant chimeric molecules which retain the desired activity. If an enzyme activity is the desired activity, then a selection assay can be designed for it. The selection of the desired molecule can be accomplished by various methods as the skilled worker would know. For example, selection can be accomplished by color (e.g., where cleavage by the enzyme produces an end-product having a detectable color), by conferring resistance to clones expressing an active enzyme (e.g., drug resistance), etc. In one embodiment, screening is performed by plating a library on solid medium, adding a chromogenic or fluorogenic substrate, and observing product development in individual colonies. In vivo selection can be applied when the molecule is necessary for growth in the presence of antibiotic (antibiotic resistance; this technique is used with the beta-lactamase in the examples), or when the activity is used for complementation of an missing essential gene in auxotrophic bacteria (e.g., auxotrophy for an amino acid). In vitro selection can also be used when the enzyme is displayed on phage; e.g., WO 93/11242.

To measure the activity of the selected enzymes, any classical spectrophotometric, fluorometric, potentiometric (pHstat) technique can be used. In the particular, the ORIGEN™ technology (IGEN Gaithersburg, Md.) can be used for detection of product formation (Liang et al., *J. Am. Chem. Soc.*, 118:9198–9199, 1996; Liang et al., *Anal. Chem.*, 68:2426–2431, 1996). A next step of selection is to identify clones which bind to the binding molecule. In one embodiment, the chimeric target molecule is expressed on a phage. Selection can be accomplished by antibody panning technique, column chromatography, etc. See, e.g., Grihalde et al., *Gene*, 166:187–195 (1995); McNally et al., *J. Bio. Chem.*, 270:19744–19751, 1995; O'Neil and Hoess, *Curr. Opin. Struct. Biol.*, 5:443–449, 1995. In another aspect of the invention, substrate elution is utilized to identify an activity of a chimeric target molecule which is inhibited by antibody binding. For example, a chimeric enzyme (e.g., displayed on a phage) having a desired mimotope is selected by its ability to be recognized by an antibody specific for the mimotope. To identify a chimeric enzyme whose activity is inhibited by the antibody, the chimeric enzyme is eluted from the antibody by the addition of an appropriate substrate. In another embodiment, the chimeric target molecule is expressed on the surface on the host cell (e.g., a bacteria, a insect cell, a mammalian cell) and selection can be accomplished without cell lysis. The chimeric target can also be expressed within the host cell and selection accomplished after, e.g., permeabilizing or lysing the cells, or otherwise making the expressed product accessible to the binding molecule.

A chimeric target molecule can be used to detect the presence or amount of an analyte in test sample. In one embodiment, a chimeric TM is a chimeric enzyme. The chimeric enzyme is contacted with a (1) test sample containing an analyte, and (2) a substrate upon which the chimeric TM enzyme catalytically acts, to form a reaction mixture. The amount of analyte present in the reaction mixture is determined by monitoring or detecting the amount of catalysis on the substrate achieved by the chimeric enzyme, wherein the analyte modulates the catalysis by the chimeric enzyme. A test sample can be any sample containing an analyte whose presence or amount it is desired to be known, e.g., body fluids such as blood, serum, urine, feces, or lymph, tissue homogenates, biopsies, organ fluids, tissue culture medium, etc. By "analyte," it is meant a molecule whose presence in a test sample is being detected. In one embodiment, the analyte is an antibody, such as an antibody specific for prostate specific antigen (PSA), carcinoma embryonic antigen (CEA), c-erbB2, products of oncogenes, viral (HIV or hepatitis), bacterial (staphylococcal), and the chimeric TM is a chimeric enzyme. Binding or attachment of the antibody or BM to the chimeric enzyme can modulate catalysis on the substrate by the chimeric enzyme. Modulation of activity is discussed above. In a preferred example, the enzyme activity of the chimeric enzyme is reduced (inactivated) by the antibody. Thus, the presence of the analyte antibody in the test sample can be determined by monitoring or detecting the reduction of activity manifested by the chimeric enzyme, either as individual molecules or as a population. Alternatively, the analyte is a polypeptide such as any of the aforementioned proteins or fragments thereof. When the chimeric molecule is combined with an appropriate binding molecule, its activity is modulated.

In another aspect of the present invention, the activity of a reaction mixture, comprising a chimeric enzyme and a binding molecule (BM) which modulates the activity of the chimeric enzyme, can be further affected by an analyte (a ligand of the binding molecule). The analyte can act as a direct competitor of the interaction of the chimeric enzyme with BM: addition of the analyte competes or displaces the binding molecule from TM, reversing its modulatory effect on the detectable activity. In one embodiment, the binding molecule inactivates the chimeric TM; addition of the analyte will result in the restoration of activity in the reaction mixture.

The enzyme assay can be performed in accordance with known procedures. For example, the activity can be monitored temporally, kinetically, or by end-point. The chimeric enzyme can be in solution or on a solid support, e.g., directly coupled or via biotin-streptavidin coupling, to materials such cellulose, Sephadex, plastics, polypropylene, polystyrene, polyvinyl, cellulose nitrate, polyethylene, nylon, polymethylmetacrylic, etc. The coupling can be accomplished as one having skill in the art would know. See, e.g., *Methods in Enzymology*, Volume 73, for various techniques on substrates, coupling, and assays in general. By the term "contacting" the chimeric molecule with a test sample containing analyte or binding molecule, it is meant that the analyte or binding molecule is brought into contact with the chimeric molecule by a desired means. The contact can be accomplished by: adding a test sample to a solution containing the chimeric TM, dipping a solid support containing the chimeric enzyme into a solution containing the analyte or BM, dropping a solution containing an analyte on to a solid support containing the chimeric TM, etc. If a substrate is used, e.g., where a chimeric TM is an enzyme, the substrate can be contacted with the chimeric enzyme at the same time as the analyte, or before or after, i.e., simultaneously or sequentially.

As mentioned, the chimeric TM can be any molecule having a desired activity, e.g., enzymatic, fluorescent, activating, complementary, etc. Assays for detecting an analyte can be tailored as one of ordinary skill in the art would know for monitoring or detecting the change in activity of the selected chimeric TM.

In another aspect of the present invention, an analyte is a competitor of a binding molecule. The presence or amount of competition with the binding molecule is used to ascertain its presence. An example of such a process is described in Example 2. A chimeric molecule (in the example, it is β-lactamase) having a mimotope recognized by a antibody specific for a desired molecule is prepared (in the example, it is prostate-specific antigen or "PSA"). Binding of the antibody to the mimotope reduces the activity of the chimeric molecule. The analyte (in the example, it is PSA) competes with the antibody for binding to the mimotope. Thus, if analyte is present, less of the antibody binds to the chimeric molecule. With less antibody bound to the chimeric molecule, the chimeric molecule is more active than in the absence of the analyte.

The assays of the present invention are useful for medical, veterinary, environmental, and various diagnostic uses, e.g., for detecting diseases, pathogenic disorders, environmental contamination, tissue culture contamination, etc. For example: the presence of cancer in a patient can be determined by detecting the presence of a characteristic antigen or antibody. It is known that individuals with cancer can have elevated levels of various antigens, such as prostate-specific antigen (PSA) or carcinoma embryonic antigen (CEA).

For other aspects of the nucleic acids, polypeptides, antibodies, etc., reference is made to standard textbooks of molecular biology, protein science, and immunology. See, e.g., Davis et al. (1986), *Basic Methods in Molecular Biology*, Elsevier Sciences Publishing, Inc., New York; Hames et al. (1985), *Nucleic Acid Hybridization*, IL Press, *Molecular Cloning*, Sambrook et al.; *Current Protocols in Molecular Biology*, Edited by F. M. Ausubel et al., John Wiley & Sons, Inc; *Current Protocols in Human Genetics*, Edited by Nicholas C. Dracopoli et al., John Wiley & Sons, Inc.; *Current Protocols in Protein Science*; Edited by John E. Coligan et al., John Wiley & Sons, Inc.; *Current Protocols in Immunology*; Edited by John E. Coligan et al., John Wiley & Sons, Inc.

THE DRAWINGS

FIGS. 1a, 1b and 1c show the insertion sites used to generate lib1 and lib3 libraries: lib1 1. V103, 2. E104 and 3. Y105; lib3: 4. T271 and 5. M272; catalytic site 6. S70.

FIG. 3 is a curve showing an expanded area of FIG. 2, representing the enzyme activity as a function of psa19, between 0 and 50 nM.

EXAMPLES

Example 1

Figure 1A:
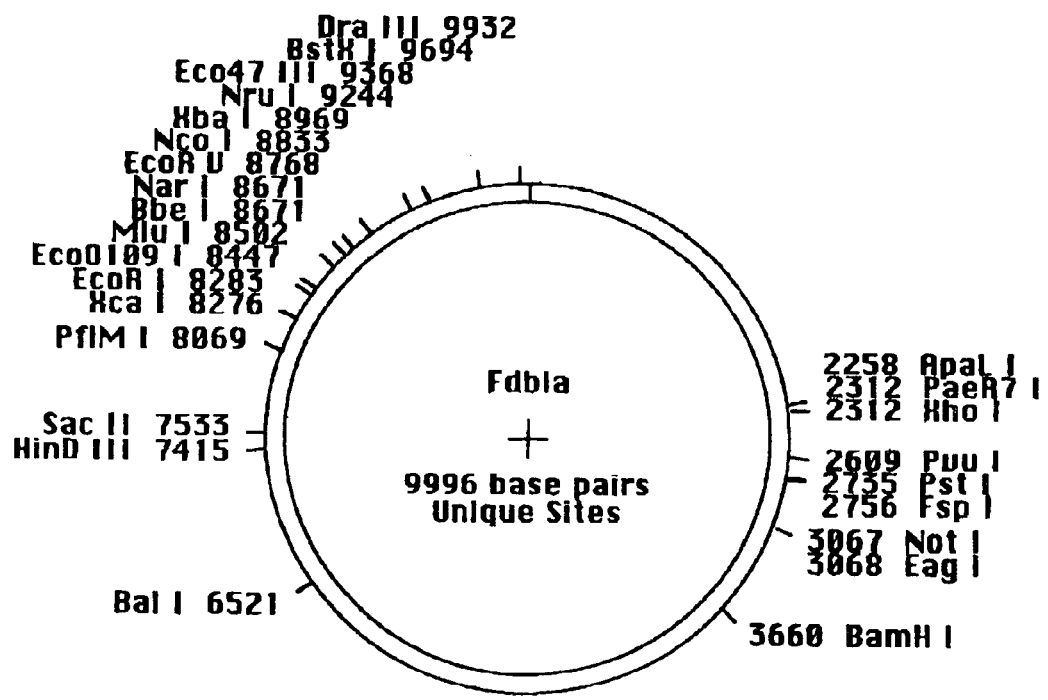

Construction of the libraries. The filamentous fd phage carrying the β-lactamase gene in fusion with the coat protein pIII (fdBla$^+$) was described in Soumillion, P., Jespers, L., Bouchet, M., Marchand-Brynaert, J., Winter, G. and Fastrez, J. Selection of β-lactamase on Filamentous Bacteriophage by Catalytic Activity. J. Mol. Biol. 237, 415–422 (1994). The restriction map of the phage is given in FIG. 1a; the DNA sequence of the R-Tem β-lactamase gene inserted between the ApaLI and NotI restriction sites engineered within the phage gene 3 is given in FIG. 1b together with the encoded amino acid sequence. Three libraries, lib1, lib2 and lib3, were constructed by introducing into the fdBla$^+$ plasmid unique restriction sites on either sides of the regions to randomize (by site directed mutagenesis) and by cloning, between these sites, small partially degenerated DNA fragments. The inserts were produced by synthesizing oligonucleotides of the desired sequences and by converting them to double strand DNA by the elongation of a small primer hybridizing to the 3' non-degenerated part of the oligonucleotides. The lib4 library was constructed by exchanging an EcoRI-PvuI restriction fragment of the fdBla$^+$ plasmid covering the lib1 mutations, for the corresponding non-mutated fragment of the fdBla$^+$ plasmid into the lib3 library. The DNA libraries were electroporated into the TG1 strain of *E. Coli*. Additional details are given below.

Phage-enzyme stock preparations. The phage-enzyme libraries were produced by spreading electrotransformed bacteria on large 530 cm$^2$ plates containing solid LB medium and tetracycline at 7.5 μg/ml. Transformants were allowed to grow for 20 h. at 37° C. and then were recovered by washing the plates with LB medium. The bacteria were discarded by centrifugation and the phages purified from the supernatants by PEG/NaCl precipitations. To increase the average number of β-lactamases displayed per phage, the phage libraries were reamplified in liquid medium at 23° C. just before selecting them on mAbs (1 β-lactamase is displayed per phage at 23° C. compared to 0.2 β-lactamase per phage at 37° C., data not shown). Libraries that were selected for activity were produced in the same conditions except that they were plated on plates containing ampicillin (at 10 μg/ml or at 30 μg/ml). Individual clones were always amplified at 23° C. in liquid LB medium.

Enzyme assays. The β-lactamase activity on phage was assayed in solution at 20° C. in 50 mM Na phosphate buffer at pH 7.5. Except when otherwise noted, benzyl-penicillin (PenG) was used as substrate. The decrease in absorbance was measured at 232 nm as a function of time to afford the values of kcat expressed in $s^{-1}$ per mole of phage-enzymes.

Example 2

1. Construction of a Library in a Loop on the Rim of the Active Site of the β-Lactamase Protein (lib1).

Figure 1C:
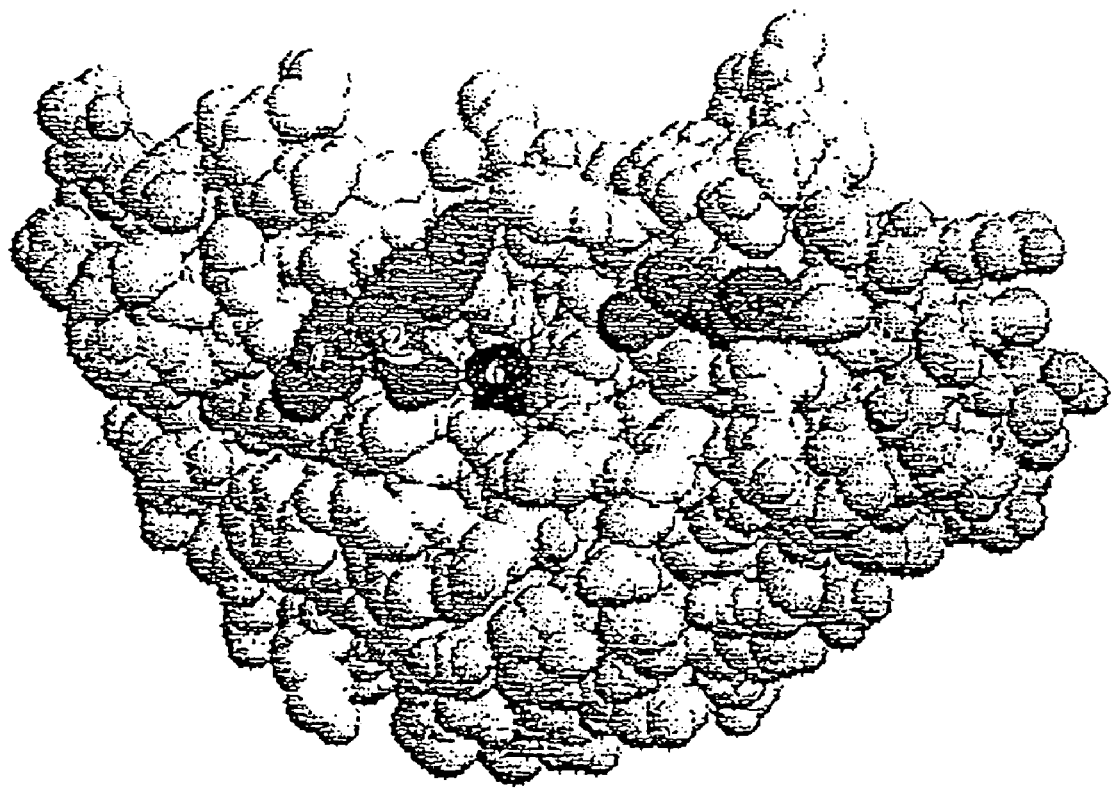

Random peptide sequences have been inserted in the region 103–105 of the sequence of the R-Tem β-lactamase (J. G. Sutcliffe, *Proc. Natl. Acad. Sci.*, 75:3737–3741, 1995). The loop on the rim of the active site, in the region encompassing V103–V105, was chosen as an insertion-replacement site because its position is close to the catalytic pocket and the sequence is poorly conserved in this region among class A β-lactamases. See FIG. 1c.

Two different lib1 libraries, lib1A-B and lib1D have been constructed on the basis of an inactivated vector. They both contain a six amino acid insert in replacement of residues E104–Y105 and V103–Y105, respectively. The theoretical size of these libraries is 64,000,000 different sequences. The inactivated vector (fdBlaI1) was produced by site directed mutagenesis of fdBla+ sing the phosphorothioate method (Nakamaye, K. C. and Eckstein, F. (1986) Nucl. Acid Res. 14, 9679–9688). This vector features two new restriction sites, BbsI and SgrAI, and a stop codon inactivating the enzyme (scheme 1a).

Scheme 1a: sequence of fdBlaI1 between codons 100 and 109 of the β-lactamase gene (restriction sites are underlined, the base inserted to introduce stop codon is in bold, encoded residues are shown below the DNA sequence):

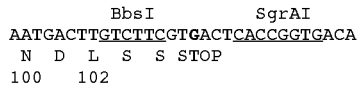

Two double stranded oligonucleotide cassettes were prepared as shown in scheme 1b and 1c by annelation of a small primer on the 3' non-degenerated part of the synthetic oligonucleotide containing the random sequences, elongation of the primer catalyzed by T4 polymerase and purification on 15% polyacrylamide.

Scheme 1b: sequence of the oligonucleotide containing the random cassette and the primer:

```
5'-
AGCCAATGGCCGGCGA(MYY)6AACCAAGTCAGCGTCTTCGAGTTTCG-3'
                                   3'-CGCAGAAGCTCAAAGC-5'
```

Scheme 1c: double stranded cassette for lib1A-B construction (the restriction sites are underlined, cleavage sites for BbsI are indicated by arrows.)

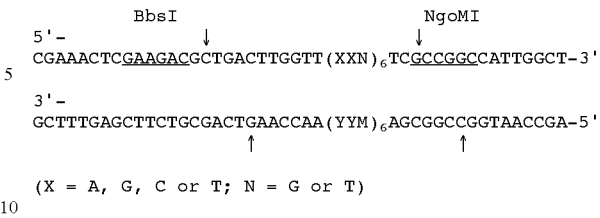

(X = A, G, C or T; N = G or T)

The vector was restricted with BbnsI and SgrAI and agarose purified. The cassette was restricted with BbsI and NgoMI. A tenfold excess of the cassette was then ligated with the vector. The contaminating fdBlaI1 vector was removed by BbsI digestion. The product was resuspended in 100 μl of buffer in preparation for electroporation. Twice, 4 μl of this ligation mixture was used to transform competent TG1 cells to produce the libraries lib1A and lib1B. Samples of these libraries were plated on solid LB medium containing 10 μg/ml tetracycline, allowing determination of the number of clones obtained per 4 μl electroporation, i.e.: $1.8 \times 10^6$ and $4.7 \times 10^6$ clones for lib1A and lib1B respectively. The activities of the lib1A-B libraries were evaluated by plating samples of bacteria on plates with different ampicillin concentrations and counting the clones obtained after incubation at 37° C. or 23° C. These titrations permitted the determination of the conditions to unambiguously select clones with activities higher than 30–40 $s^{-1}$ (i.e., incubation at 37° C. for 17 hours on LB plates containing 10 μg/ml of freshly dissolved ampicillin). The activities of the libraries are low since only 0.05% and 0.08% of their clones are able to grow on 10 μg ampicillin/ml at 37° C. Activity measurements carried out on several individual clones selected in those conditions confirmed this activity. See Table 1. Several individual clones have been sequenced. The sequence variability is moderate and clones with shortened sequences are present. This was observed despite the fact that the degenerated oligonucleotides used to construct the inserts were purified on acrylamide. The purification step is efficient but insertions are probably not well tolerated in this region, consequently, the rare active clones corresponding largely with shortened sequences are selected.

The active fractions of the lib1A-B libraries have been produced on a large scale (=lib1C$_2$ and lib1C$_4$). Lib1A-B should contain $6.4 \times 10^7$ times 0.05%–0.08% clones growing on 10 μg/ml ampicillin containing plates, i.e., between 32,000 and 51,000 clones. Our purpose is to produce the complete phage and DNA libraries. The latter will be used to create the recombination library lib4. To produce enough material for isolation of the DNA library, two rounds of plating on large dishes were necessary. In the first round, the product of fourteen 4 μl electroporations was plated after dilution in 52 ml of Soc medium onto two 23×23 cm dishes (solid medium containing 10 μg/ml of tetracycline and 10 μg/ml of ampicillin.) After 18 hours growth at 37° C., the bacteria were collected in 120 ml of liquid LB medium. A 60 fold dilution of the cell's solution diluted to an optical density at 600 nm of 0.5 was plated on ten large dishes to produce 79,000 clones (libC2). The experiment was repeated and 150,000 clones were obtained (libC4). From these, phage and DNA libraries were prepared, respectively, as described in example 1 and by conventional methods (Sambrook et al. (1989) Molecular cloning: A laboratory Manual. 2nd Edit., Cold Spring Harbor Laboratory). A few individual clones were produced in quantity to measure their activity and determine their sequence. See Table 2.

The same protocols were used to produce library Lib1D. A cassette was constructed by conversion of the autohybridizing oligonucleotide shown in scheme 1d into its double stranded form (scheme 1e).

Scheme 1d: sequence of the auto-hybridizing oligonucleotide containing the random cassette

```
        NgoMI                   BbsI     BbsI
5'-GGGAGGGAAGCCGGCGA(YNN)₆CAAGTCAGGGTCTTCGAAGACCCTG
```

Scheme 1e: double stranded cassette for lib1A-B construction: the restriction sites are underlined, the cleavage sites for BbsI and NgoM1 are indicated by arrows.

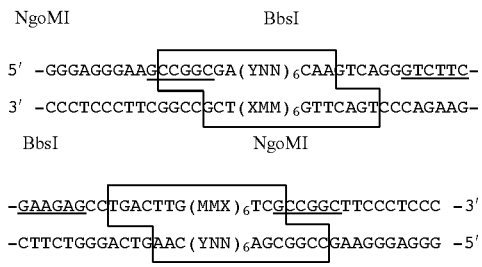

After purification and restriction by BbsI and NgoMI, this cassette was ligated into the restricted and agarose purified vector fdBlaI1. The contaminating cloning vector was removed by BbsI digestion and the ligation mixture was used for the transformation of TG1 cells by electroporation. 3 μl afforded 9.2×10⁶ transformants among which 0.11% produced an enzyme active enough to grow on a medium containing 10 μg/ml Amp. The complete library (lib1D2) was produced as described for lib1C2 and lib1C4. The activity and sequence of a few clones were determined. See Table 3.

TABLE 1

Sequences and activities of lib 1 A clones selected on 10 μg ampicillin/ml at 37° C.

| Clones | Inserted Sequence | | | | $Kcat\ (s^{-1})^a$ |
|---|---|---|---|---|---|
| FdBla | $Val_{103}$ | ---- $Glu_{104}\ Tyr_{105}$ | | $Ser_{106}$ | ND |
| Lib1A-01 | | ---- Val Ser | | | 29 |
| Lib1A-02 | | --- Leu His Ser | | | 16 |
| Lib1A-03 | | Lys Ala Gly Ser Asp Gly (SEQ ID NO: 1) | | | 70 |
| Lib1A-04 | | Gly Gly Pro Arg Ser Trp (SEQ ID NO: 2) | | | 15 |
| Lib1A-05 | | Lys Asn Cys Gly Lys Cys (SEQ ID NO: 3) | | | 12 |
| Lib1A-06 | | Asp Val Pro Gly Ala Gly (SEQ ID NO: 4) | | | 47 |
| Lib1A-07 | | Lys Ser Gly Glu His Ser (SEQ ID NO: 5) | | | 145 |
| Lib1A-08 | | --- Pro Gly Gly | | | 74 |
| Lib1A-09 | | Arg Ala Gly Asn His Ser (SEQ ID NO: 6) | | | 265 |
| Lib1A-010 | | Asp Pro Pro Gly Tyr Gly (SEQ ID NO: 7) | | | 9 |

$^a$kcats from phages produced at 23° C. (PenG)
ND: not done

TABLE 2

Sequences and activities of lib1C₄ clones

| Clones | Inserted sequence | | | | $Kcat\ (s^{-1})^a$ |
|---|---|---|---|---|---|
| FdBla | $Val_{103}$ | ---- $Glu_{104}\ Tyr_{105}$ | | $Ser_{106}$ | ND |
| LibC4-11 | | Arg Phe Gly Asn Asp Trp (SEQ ID NO: 8) | | | 159 |
| LibC4-12 | | ---- Trp Trp | | | ND |
| LibC4-13 | | -- Arg Ser His Trp (SEQ ID NO: 9) | | | ND |
| LibC4-14 | | ---- Gln Trp | | | ND |
| LibC4-15 | | Asp Gln Met Gly Gly Gly (SEQ ID NO: 10) | | | ND |
| LibC4-16 | | Arg Ala Gly Ser Thr Trp (SEQ ID NO: 11) | | | 64 |
| LibC4-17 | | Lys Gly Gly Leu Glu Ser (SEQ ID NO: 12) | | | 721 |
| LibC4-18 | | ---- Ser Asn | | | ND |
| LibC4-19 | | ---- Glu Gly | | | ND |

$^a$kcats from phages produced at 23° C. (PenG)
ND: not done

TABLE 3

Sequences and activities of lib1D₂ clones

| Clones | Inserted sequence | | | | $Kcat\ (s^{-1})^a$ |
|---|---|---|---|---|---|
| FdBla | $Leu_{102}$ | --- $Val_{103}\ Glu_{104}\ Tyr_{105}$ | | $Ser_{106}$ | ND |
| Lib1D2-02 | | --- Val Gly Gly | | | ND |
| Lib1D2-03 | | --- Val Thr Tyr | | | ND |
| Lib1D2-04 | Phe | --- Gly Thr Trp | | | ND |
| Lib1D2-05 | | Leu Pro Asn Leu Asp Thr (SEQ ID NO: 13) | | | 224 |
| Lib1D2-06 | | --- Ile Ser Trp | | | ND |
| Lib1D2-07 | | Asn Arg Ser Gly Ser Trp (SEQ ID NO: 14) | | | 2506 |
| Lib1D2-08 | | Asp Val Ser Gly Gly His (SEQ ID NO: 15) | | | 337 |
| Lib1D2-09 | | Leu His Ser Gly Gly Trp (SEQ ID NO: 16) | | | ND |
| Lib1D2-10 | | Ser Arg Ala Gly Gly Tyr (SEQ ID NO: 17) | | | ND |

$^a$kcats from phages produced at 23° C. (PenG)
ND: not done

2. Construction of a Library in the Loop Preceding the α11 Helix of β-Lactamase (lib3).

The loop preceding the α11 helix (residues 271–272) of β-lactamase was chosen as an insertion site because of its position relatively close to the catalytic pocket and its poor sequence conservation among the known β-lactamases. This region is also well located with regard to the insertion site of the lib1 library (residues 103–106) for the construction of a non linear epitope. Indeed, these two regions lie on opposite edges of the active site. See FIG. 1c.

In one experiment, the amino acids $T_{271}$ and $M_{272}$ of the β-lactamase were exchanged for a degenerated sequence of 5 residues were exchanged to give the lib3d library. This library was constructed following the strategy used to construct the lib1 libraries. The inactivated vector (fdBlaI2) was produced by site directed mutagenesis of fdBla⁺ using the phosphorothioate method (Nakamaye, K. C. and Eckstein, F.

(1986) Nucl. Acid Res. 14, 9679–9688). This vector features two new BbsI restriction sites and a stop codon inactivating the enzyme (scheme 2a).

Scheme 2a: sequence of fdBlaI2 between codons 267 and 278 of the β-lactamase gene (restriction sites underlined with cleavage sites indicated, inserted base to introduce a stop codon in bold, encoded residues below the DNA sequence):

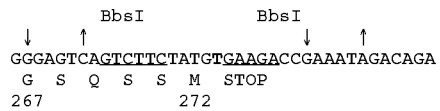

Two double stranded oligonucleotide cassettes were prepared as shown in scheme 2b and 2c by annelation of a small primer on the 3' non-degenerated part of the synthetic oligonucleotite containing the random sequences, elongation of the primer catalyzed by T4 polymerase and purification on 15% polyacrylamide.

Scheme 2b: sequence of the oligonucleotide containing the random cassette and of the primer

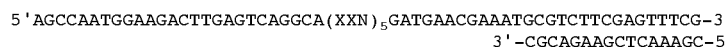

Scheme 2c: double stranded cassette for lib3d construction: the Bbs1 restriction sites are underlined, the cleavage sites are indicated by arrows.

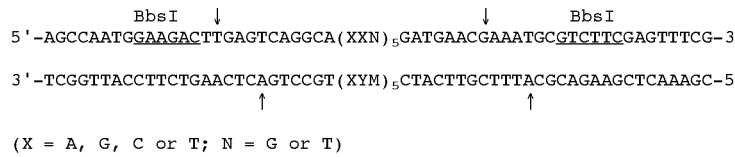

(X = A, G, C or T; N = G or T)

The vector and the cassette were restricted with BbsI. A tenfold excess of the cassette was then ligated with the vector. The contaminating fdBlaI2 vector was removed by BbnsI digestion. The product was resuspended in 100 μl. 4 μl of this ligation mixture were used to transform competent TG1 cells and produce the libraries lib3d. Samples of these libraries were plated on solid LB medium containing 10 μg/ml tetracycline to determine the number of clones obtained per 4 μl electroporation i.e.: 4.5×10$^5$ clones. The activities of the library was evaluated by plating samples of transformed bacteria on plates with different ampicillin concentrations and counting the clones obtained after incubation at 37° C. or 20° C. From 2 to 3 percent of the clones proved to be active, i.e. about 8×10$^4$ different clones. The methionine at position 272 is strongly conserved in active clones. See Table 4. About one third of the clones selected on 10 μg ampicillin contained sequences shorter than 5 residues. This results from the presence during the cloning of the degenerated insert into the β-lactamase vector of a small percentage of shortened double strand oligonucleotide; shorter insert clones are afterward strongly selected since they are more active.

Although the lib3d library was sufficiently large and active to be recombined with lib1, its variability suggested the construction of a second library in the same region but replacing only residue $T_{271}$. The size of the insert was increased to 6 amino acids, instead of 5, in order to take into account the more remote position of the new insertion site. The lib3f library was constructed like lib3d by cloning a cassette into the fdBlaI2 vector, the cassette is shown in scheme 2d.

Scheme 2d: double stranded cassette for lib3f construction: the BbsI restriction sites are underlined, the cleavage sites are indicated by arrows.

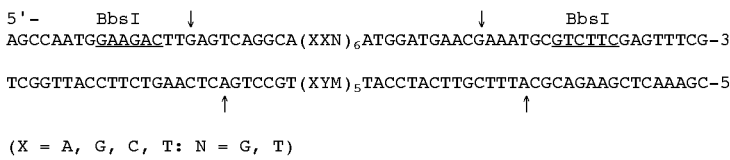

(X = A, G, C, T: N = G, T)

Transformation of TG1 with 4 μl of ligation mixture afforded 7.0×10$^6$ clones.

The library produced, lib3f, was very active since about 7% of the clones were able to grow on 10 μg ampicillin/ml at 37° C. Sequencing of several clones selected in those conditions indicated that active clones have a wide sequence variability and do not contain shortened insertion sequences. See Table 5. This results from the fact that the degenerated oligonucleotides were purified on acrylamide gel.

The active fractions of the lib3f library were prepared by electroporating 3 times 100 μl of TG1 cells with 6 μl of litigation mixture and diluting first to 12 ml of Soc medium, then to 48 ml of LB medium. The bacteria were plated on 10 large dishes (23×23 cm) and grown for 18 hours at 37° C. The libraries were then recovered from plates with 3 times 20 ml of LB medium at 4° C. The bacteria were centrifugated and the double stranded DNA was extracted by usual methods and purified on CsCl gradients to afford large DNA stocks; the phages were purified from the supernatant (=lib3G). The size of the libraries, about 4×10$^6$ different active clones, and the activity of the lib3G library should allow direct affinity selections with psa antibodies (see below). Lib3d was handled similarly to produce the active library lib3E.

TABLE 4

Sequences and activities of several clones from the lib3d library picked from among the 3% most active ones

| Clones | | Inserted sequence | | | Kcat (s$^{-1}$)$^a$ |
|---|---|---|---|---|---|
| FdBla | Ala$_{270}$ | --- Thr$_{271}$ Met$_{272}$ | Asp$_{273}$ Glu$_{274}$ Arg$_{275}$ | | ND |
| Lib3-01 | | --- SerMet | | | 1133 |
| Lib3-02 | | -- Ala Thr Thr | | | 203 |
| Lib3-03 | | Thr Ala Lys Met Asp (SEQ ID NO: 18) | | | 127 |
| Lib3-04 | Pro | Pro Thr Val Ser Met (SEQ ID NO: 19) | | | 92 |
| Lib3-05 | | Arg Gln Ser Thr Met (SEQ ID NO: 20) | | | 48 |
| Lib3-06 | Asp | -- Asp Arg Ala | | | 1.1 |
| Lib3-07 | | Gly Arg Thr Thr Met (SEQ ID NO: 21) | | | 44 |
| Lib3-08 | | Ser Asp Gln Pro Leu (SEQ ID NO: 22) | Leu | | 140 |
| Lib3-09 | | His Thr Ala Ser Met (SEQ ID NO: 23) | | | 137 |
| Lib3-10 | | --- Asn Gly | | | 278 |
| Lib3-11 | | Lys Ser Val Gly Leu (SEQ ID NO: 24) | | | ND |
| Lib3-12 | | Ala Asn Ile Ser Leu (SEQ ID NO: 25) | | | ND |
| Lib3-13 | | --- Asn Ile | | | ND |
| Lib3-14 | | Pro Val Ala Pro Ile (SEQ ID NO: 26) | | | ND |
| Lib3-15 | | Arg Pro Thr Thr Leu (SEQ ID NO: 27) | | | ND |
| Lib3-16 | | Pro Asn Ala Asn Met (SEQ ID NO: 28) | | | ND |
| Lib3-17 | | -- Ala Thr Thr | | | ND |

$^a$kcats from phages produced at 23° C. (PenG)
ND: not done

TABLE 5

Sequences and activities of lib3f clones selected on 10 μg ampicillin/ml at 37° C.

| Clones | | Inserted sequence | | Kcat (s$^{-1}$)$^a$ |
|---|---|---|---|---|
| FdBla | Ala$_{270}$ | ----- Thr$_{271}$ | Met$_{272}$ Asp$_{273}$ Glu$_{274}$ Arg$_{275}$ (SEQ ID NO: 40) | ND |
| Lib3-18 | | Ala Thr Ser Phe Ala Pro (SEQ ID NO: 29) | | 208 |
| Lib3-19 | | Arg Arg Lys Gln Pro Thr (SEQ ID NO: 30) | | 32 |
| Lib3-20 | | Thr Ala His Val Ala Ser (SEQ ID NO: 31) | | 99 |
| Lib3-21 | | Thr Asn Lys Gln Pro Ser (SEQ ID NO: 32) | | 73 |
| Lib3-22 | | Lys Ser Tyr Thr Pro Glu (SEQ ID NO: 33) | Gln | 85 |
| Lib3-23 | | Lys Trp Asn Tyr Thr Thr (SEQ ID NO: 34) | | ND |
| Lib3-24 | | Gly Glu His Glu Ala Gly (SEQ ID NO: 35) | | 114 |
| Lib3-25 | | Glu Glu Asn Gly Arg Pro (SEQ ID NO: 36) | Gln | 100 |
| Lib3-26 | | Gln Leu Gln Val Pro Pro (SEQ ID NO: 37) | | 186 |
| Lib3-27 | | Ala Pro Gly Asn Asp Gly (SEQ ID NO: 38) | | 64 |
| Lib3-29 | | Ala Gly Ala Thr Tyr Glu (SEQ ID NO: 39) | | 111 |

$^a$kcats from phages produced at 23° C. (PenG)
ND: not done

3. Recombination of the lib1 and lib3 Libraries.

The libraries (lib1C2, 1C4 and 1D2 in the 103–105 region, and lib3E and 3G in the 271–272 region) were selected on ampicillin and contain essentially clones whose kcats are higher than 40 s$^{-1}$ (i.e., ≧4% of wild type activity). The size of the lib1 and lib3 libraries are about 1×10$^4$ and 4×10$^6$ clones, respectively.

A further selection of the lib3G library on ampicillin was carried out before recombining it with the lib1 library. The lib3G is very large and has a wide diversity of sequences so that only the most active clones were selected. This is expected to increase the chances of obtaining an active recombinant library. The lib3G library was selected on 30 μg ampicillin/ml at 37° C., which permitted selection of 10% of its clones. In this way, the activity of the library was increased by a factor of 1.5.

To construct the recombinant library, the lib1C2, 1C4 and 1D2 libraries were pooled and were recombined with the lib3H library. The pooled lib1 libraries above and the lib3H library were digested with EcoRI and PvuI. The library of large fragments derived from lib1 and the library of small fragments derived from lib3H were purified on gel, ligated, and used for transformations. The library (rec1) was very active as about 20% of its clones were able to grow on 10 μg ampicillin/ml at 37° C. This means that 20% of its clones have activities higher than 40 s$^{-1}$. The sequencing of these clones showed that only 2 clones/13 contained simultaneously a full insert in both locations. See Table 6. This frequency results from the presence in the lib1 library of about 50% of shortened inserts. To determine the activities of the correctly-constructed clones, the kcats of several clones not selected on ampicillin were measured. Among 12 clones analyzed only 2 had activities lower than 10 s$^{-1}$. See Table 7. It appears that the well-constructed clones possess relevant activities even though the majority of them are probably unable to grow on 10 μg ampicillin/ml.

Several different cloning approaches were taken to obtain a recombinant library of great size. The best library was produced on a large scale (=lib rec4b) and contains about 5×10$^7$ different clones. This library was not submitted to any further treatment before selection on psa antibodies. Selection on ampicillin can be used to amplify the proportion of well-constructed clones.

TABLE 6

Sequences and activities of rec 1 clones selected on 10 μg ampicillin/ml at 37° C.

| Clones | Inserted Sequence | | Kcat(s⁻¹)ᵃ |
|---|---|---|---|
| FdBla | Leu$_{102}$ — — — Val$_{103}$ Glu$_{104}$ Tyr$_{105}$ Ser$_{106}$ — — — Ala$_{270}$ | — — — — — Thr$_{271}$ Met$_{272}$ | ND |
| Rec 1-01 | Glu Arg Ser Gly His Trp (SEQ ID NO: 41) | — — — — — Thr | 145 |
| Rec 1-03 | — — — Val Glu Tyr | Arg Thr Ala Lys Val Ser (SEQ ID NO: 44) | 57 |
| Rec 1-04 | — — — Val Thr Trp | Gln Lys Val Glu Pro Ser (SEQ ID NO: 45) | 61 |
| Rec 1-05 | — — — Val Leu Gly | — — — — — His | 145 |
| Rec 1-06 | — — — Val Gln Gly | Thr Gly Val Tyr Pro Ser (SEQ ID NO: 46) | 170 |
| Rec 1-07 | — — — Cys Met Gly | Gln Gly Pro Trp Ala Ser (SEQ ID NO: 47) | 380 |
| Rec 1-09* | — — — Ile Glu Gly | Ile Gly Asp Tyr Ser Lys (SEQ ID NO: 48) | 251 |
| Rec 1-10 | — — — Val Asp Trp | Thr Gly Asn Gln Ala Thr (SEQ ID NO: 49) | 93 |
| Rec 1-11* | — — — Val Ser Gly | Ser Asn Gly Glu His Ser (SEQ ID NO: 50) | 54 |
| Rec 1-12 | — Leu Ala Ser Gly Tyr (SEQ ID NO: 42) | Ser Gly His Glu Pro Thr (SEQ ID NO: 51) | 139 |
| Rec 1-14 | — — — Val Pro Tyr | Asp Ser Lys Glu Thr Ser (SEQ ID NO: 52) | 304 |
| Rec 1-15* | Val Arg Ser Gly Pro Trp (SEQ ID NO: 43) | Thr Ala Arg Trp Ala Asn (SEQ ID NO: 53) | 72 |
| Rec 1-16 | — — — Val Met Gly | Thr Ala Asn Glu His Thr (SEQ ID NO: 54) | 155 |

ᵃkcats from phages produced at 23° C. (PenG)
ND: not done
*clones containing an additional mutation (Arg$_{275}$$^L$)

TABLE 7

Activities of rec 1 clones not selected on ampicillin.

| clones | kcat(s⁻¹)ᵃ |
|---|---|
| rec 1-17 | 57 |
| rec 1-18 | 12 |
| rec 1-19 | 187 |
| rec 1-20 | 32 |
| rec 1-21 | 32 |
| rec 1-22 | 1.8 |
| rec 1-23 | 15 |
| rec 1-24 | 224 |
| rec 1-25 | 67 |
| rec 1-26 | 155 |
| rec 1-27 | 4.6 |
| rec 1-28 | 20 |

ᵃkcats from phages produced at 23° C. (PenG)

Example 3

1. Selection for Binding by Monoclonal Antibodies psa10 and psa66.

Three rounds of selection were carried out on the lib3j (prepared by pooling the lib3E, lib3G(a) and lib3G(b) libraries) and rec4B libraries by panning on streptavidin-coated magnetic beads (Dynabeads M280 from Dynal AS, Oslo, Norway) saturated with biotinylated psa10 and psa66 antibodies as selecting agents (from CanAg Diagnostics AB, Gothenburg, Sweden). The phages displaying mutant β-lactamases with high affinity for the antibodies were extracted from these libraries. In each case an amplification factor higher than 1000-fold was obtained between the first round of selection and the third one (ratio of the number of phages eluted between the 3rd and 1st round of selection—elution at low pH or by substrate addition). This indicates that an efficient selection was achieved.

The effect of the mAbs on the activity of the enzymes was determined after incubation of the phage-enzymes with various mAb concentrations for at least 10 minutes before adding the substrate. The rates of hydrolysis were always determined in conditions where the substrate concentration is at least 3 times higher than the $K_m$ of the modified enzymes, bound or not to their respective mAb. The dissociation constants between the enzymes and the mAbs were determined from the inhibition curves presented in FIG. 2 on the basis of the following equations:

$$[E.mAb]^2 - [E.mAb]([E]_t + [mAb]_t + kd) + [E]_t[mAb]_t = 0$$

$$kcat\ obs. = kcat\ E - ([E.mAb]/[E]_t)(kcat\ E - kcat\ E.mAb)$$

where $[E]_t$ and $[mAb]_t$ are the total enzyme and antibody concentrations respectively, [E.mAb] is the enzyme-mAb complex concentration, kd is the dissociation constant of the enzyme-mAb complex, kcat E and kcat E.mAb are the catalytic constants of the free enzyme and the complex.

After the third round of selection, the effect of psa antibody binding on activity on PenG as substrate was determined on the libraries selected; a slight inhibition was observed in the case of the psa66-selected rec4b library (~20 at 3.3 10⁻⁷M of psa66). This inhibitory effect reached 40–45% when larger substrates (PADAC or Centa) were used.

The characterization of the phages eluted from the third round of selection indicated that a strong selection was exerted on the lib3 region of the libraries. Only a low sequence variability was observed at this location. See Tables 8 and 9. No sequence conservation could be found in the lib1 region. This region might nevertheless contribute to the binding of the antibody as the wild type residues are replaced in these clones. It is believed, however, that the psa10 and psa66 epitopes are probably linear. In the case of the phages selected on psa66, a $SX_{(1-0)}L/IQ$ consensus motif could be derived. This motif was also present in clones isolated previously from a library created in the ω-loop (lib2) after selection on the same antibody. This motif is not found in the psa sequence. With psa66, a mimotope has been selected. An HPQ sequence was found in several clones selected on psa10. This suggests that the selection was carried out, at least partially, on streptavidin instead of on the antibody. As a slight precipitate was visible in the biotinylated preparation of psa10, it is possible that the antibody was denatured and did not coat the streptavidin beads. Whether the activity of the lib3j and rec4b libraries, selected on psa10, could be regulated by streptavidin binding was tested, but no positive results were obtained. A faint stimulation in the case of the rec4b library was observed.

Several individual clones selected on psa66 from the lib3j and rec4b libraries have been analyzed. They all possess high activities. See Table 9. Whereas no regulation was found in the case of the clones isolated from the lib3j library. The clones selected were quite diverse as the sequence in the lib1 region is variable and the level of modulation depended on the clones but ranged mainly between 30 and 60% of inhibition on PADAC (R. N. Jones et al., *Clin. Microbiol.*, 15:677–683, 1982) or Centa (R. N. Jones et al., *Clin. Microbiol.*, 15:954–958, 1982) (at $3.3 \times 10^{-7}$ M of psa66). This percentage can be as high as 70% or more when the concentration of psa66 is increased to $1.7 \times 10^{-6}$ M. The inhibition is less important when PenG is used as a substrate. It is believed that the difference of behavior results probably mainly from the difference in size of the substrates, the larger substrates being less rapidly hydrolysed in the presence of the bound antibody. The maximum inhibition (at [psa66]=∞) has been calculated for one of the best regulated clones (p66Rb316) and reaches 68% on PADAC and 75% on Centa (kd=$1.2 \times 10^{-7}$ M). As the psa66-selected rec4b library appears to contain many different individuals it cannot be excluded that better regulated clones are present in it.

In the p66Rb316 clone, the wild type residues $E_{104}$–$Y_{105}$ are replaced by $T_{104}G_{105}$ and the wild type residue $T_{271}$ is replaced by DGSRQ. Unexpectedly, $R_{275}$ is mutated to $Q_{275}$. These sequences are not present in the prostate specific antigen (psa). Consequently, the monoclonal antibody recognizes a mimotope.

TABLE 8

Clones selected on psa 10.

| Clones | Inserted Sequences | | Kcat–psa66/ +psa66 $(s^{-1})$* S = PenG |
|---|---|---|---|
| FdBla | $Val_{103}$ Glu Tyr | $Thr_{271}$ Met | [psa10] = 3.3 $10^{-7}$ M |
| P10Aj3 | Library[a] | | 187/179 |
| P10Aj301 | Val Glu Tyr | His Pro Gln Asn Asp Asp Met (SEQ ID NO: 59) | ND |
| P10Aj302 | Val Glu Tyr | His Pro Gln Asn Asp Asp Met (SEQ ID NO: 60) | ND |
| P10Aj303 | Val Glu Tyr | His Pro Gln Asn Asp Asp Met (SEQ ID NO: 61) | ND |
| P10Aj304 | Val Glu Tyr | His Pro Gln Gly Asp Asn Met (SEQ ID NO: 62) His Pro Gln Gly Asp Ser Met (SEQ ID NO: 63) | ND |
| P10Aj305 | Val Glu Tyr | His Pro Gln Asn Asp Asp Met (SEQ ID NO: 64) | ND |
| P10RB3 | Library[b] | | [psa10] = 3.3 $10^{-7}$ M 52/52 |
| P10RB311 | Val Arg Tyr | Ser Asp Gly His Arg Leu Met ($Arg_{275}$→ Leu) (SEQ ID NO: 65) | ND |
| P10RB312 | Val Lys Ser Gly Val Ala (SEQ ID NO: 55) | Ser Asp Gly His Arg Leu Met ($Arg_{275}$→ Leu) (SEQ ID NO: 66) | ND |
| P10RB313 | Val Lys Ser Gly Asn Thr Trp (SEQ ID NO: 56) | Ser Asp Gly His Arg Leu Met ($Arg_{275}$→ Leu) (SEQ ID NO: 67) | ND |
| P10RB314 | Val Asp Arg Thr Lys Gly Trp (SEQ ID NO: 57) | Ser Asp Gly His Arg Leu Met ($Arg_{275}$→ Leu) (SEQ ID NO: 68) | ND |
| P10RB315 | Val Asp Gly Pro Asn Gly His (SEQ ID NO: 58) | Ser Asp Gly His Arg Leu Met ($Arg_{275}$→ Leu) (SEQ ID NO: 69) | ND |

[a]lib3j and [b]rec4b phages from the third round of selection
*kcats from phages produced at 23° C.

TABLE 9

Clones selected on psa66.

| Clones | Inserted Sequence | | Kcat-psa66/+psa66(s$^{-1}$)*; % age inhibition | | | | |
|---|---|---|---|---|---|---|---|
| | | | S = PenG | S = PADAC | | S = Centa | |
| FdBla | Val$_{103}$ Glu Thr | Thr$_{271}$ Met | [psa66] = 3.3 10$^{-7}$M | [psa66] = 3.3 10$^{-7}$M | | | |
| P66Aj3 | Library$^a$ | | 444/425; 04% | ND | | | |
| P66Aj306 | Val Glu Tyr | Thr Pro Gly Ser Leu Gln Met (Arg$_{275}$ → Leu) (SEQ ID NO: 71) | ND | 67.9/65.8; 03% | | | |
| P66Aj307 | Val Glu Tyr | Ser Ala His Gln Asp Tyr Ile (Arg$_{275}$ → Leu) (SEQ ID NO: 72) | ND | 42.4/42.4; 00% | | | |
| P66Aj308 | Val Glu Tyr | Thr Pro Gly Ser Leu Gln Met (Arg$_{275}$ → Leu) (SEQ ID NO: 73) | ND | ND | | | |
| P66Aj309 | Val Glu Tyr | Thr Pro Gly Ser Leu Gln Met (Arg$_{275}$ → Leu) (SEQ ID NO: 74) | ND | ND | | | |
| P66Aj310 | Val Glu Tyr | Thr Pro Gly Ser Leu Gln Met (Arg$_{275}$ → Leu) (SEQ ID NO: 75) | ND | ND | | | |
| | | | [psa66]= 3.3 10$^{-7}$M | [psa66] = 3.3 10$^{-7}$M | [psa66] = 1.7 10$^{-6}$M | [psa66] = 3.3 10$^{-7}$M | [psa66] = 1.7 10$^{-6}$M |
| P66RB3 | Library$^b$ | | 405/326; 20% | 23.8/14.2; 41% | ND | 12.2/6.7; 45% | ND |
| P66RB316 | Val Lys Gly | Asp Gly Ser Arg Ile Gln Met (Arg$_{275}$ → Leu) (SEQ ID NO: 76) | 182/134; 26% | 25.1/13.6; 46% | 20.5/7.8; 62% | 14.7/7.2; 51% | 15.4/4.1; 73% |
| P66RB317 | Val Lys Gly Gly His Gly Ala (SEQ ID NO: 70) | Thr Leu | ND | 28.2/26.5; 06% | ND | ND | ND |
| P66RB318 | Val Val Gly | Asp Gly Ser Arg Ile Gln Met (Arg$_{275}$ → Leu) (SEQ ID NO: 77) | ND | 28.6/11.9; 58% | ND | 13.8/5.8; 58% | 13.3/3.5; 74% |
| P66RB319 | Val Gln Gly | Asp Gly Ser Arg Ile Gln Met (Arg$_{275}$ → Leu) (SEQ ID NO: 78) | ND | 47.4/32.6; 31% | ND | ND | ND |
| P66RB321 | ND | ND | ND | 17.2/09.3; 46% | ND | ND | ND |
| P66RB322 | ND | ND | ND | 27.2/23.8; 13% | ND | ND | ND |
| P66RB323 | ND | ND | ND | 19.0/13.2; 31% | ND | ND | ND |
| P66RB324 | ND | ND | ND | 22.4/15.2; 32% | ND | ND | ND |
| P66RB325 | ND | ND | ND | 21.6/14.9; 31% | ND | ND | ND |
| P66RB326 | ND | ND | ND | 19.6/19.2; 02% | ND | ND | ND |
| P66RB327 | ND | ND | ND | 20.5/19.6; 04% | ND | ND | ND |
| P66RB328 | ND | ND | ND | 29.2/15.8; 46% | ND | ND | ND |
| P66RB329 | ND | ND | ND | 26.3/14.3; 46% | ND | ND | ND |
| P66RB330 | ND | ND | 6015/4273; 29% | 647/444; 31% | ND | 33.5/46.2; −32% | 33.2/53.7; −62% |
| P66RB331 | ND | ND | ND | 25.7/14.1; 45% | ND | ND | ND |
| P66RB332 | ND | ND | ND | 25.2/23.5; 09% | ND | ND | ND |

$^a$lib3j and $^b$rec4b phages from third round of selection
*kcats from phages produced at 23° C..

2. Selection for Binding on Monoclonal Antibody psa19.

Three rounds of selection were carried out on the lib3j library by panning using the psa19 antibody (CanAg diagnostics AB, Gothenburg, Sweden). Several clones were analyzed for regulation of activity by psa19 binding. To perform such activity assays, the phage enzyme was diluted in 50 mM phosphate buffer at pH 7, at a concentration of $2.4 \times 10^{-9}$ M. The PSA19 monoclonal antibody was added at a final concentration which varies between zero and 2.6 μM. After 10 minutes, the substrate (benzyl-penicillin) was added at a final concentration of $5 \times 10^{-4}$ M. The activity was measured by determination of the rate of decrease of the absorbance at 232 nm. A plot of the inhibitory effect of the monoclonal antibody psa19 on the catalytic activity of the mutant β-lactamase on phage identified as psa19Aj302 and extracted from the lib3j library is shown in FIGS. 2 and 3.

Figure 2:
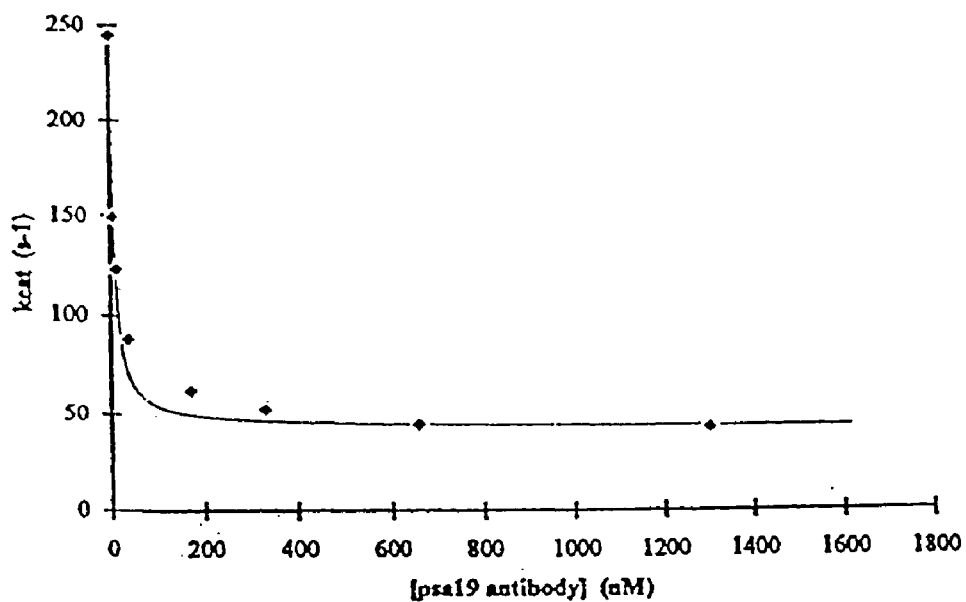
FIG. 2 and FIG. 3 are curves showing the inhibitory effect of antibody psa19 on a mutant β-lactamase psa19A;302.
Figure 3:
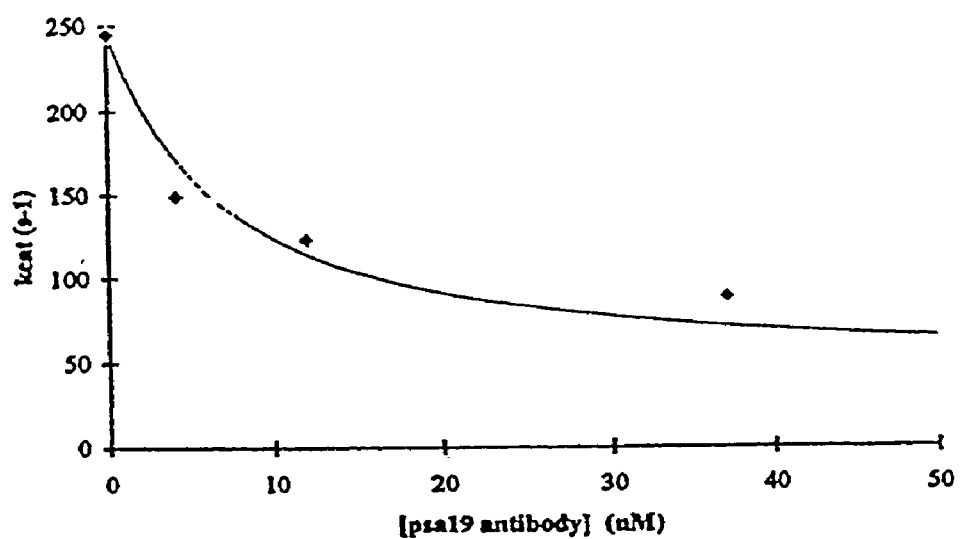

FIG. 3 is an expanded version of FIG. 2. It represents the activities as a function of [psa19] between 0 and 50 nM. The activity is reduced to 60% at a psa 19 antibody concentration of $4 \times 10^{-9}$ M and to 17% at saturation. This allows detection of the analyte PSA itself at a nM concentration by observation of an increase in activity.

In the psa19Aj302 clone, the wild type residue $T_{271}$ was replaced by SWPVKS. Unexpectedly, $R_{275}$ was also mutated to $Q_{275}$. These sequences are not present in PSA. Thus, the monoclonal antibody recognizes a mimotope.

Figure 4:
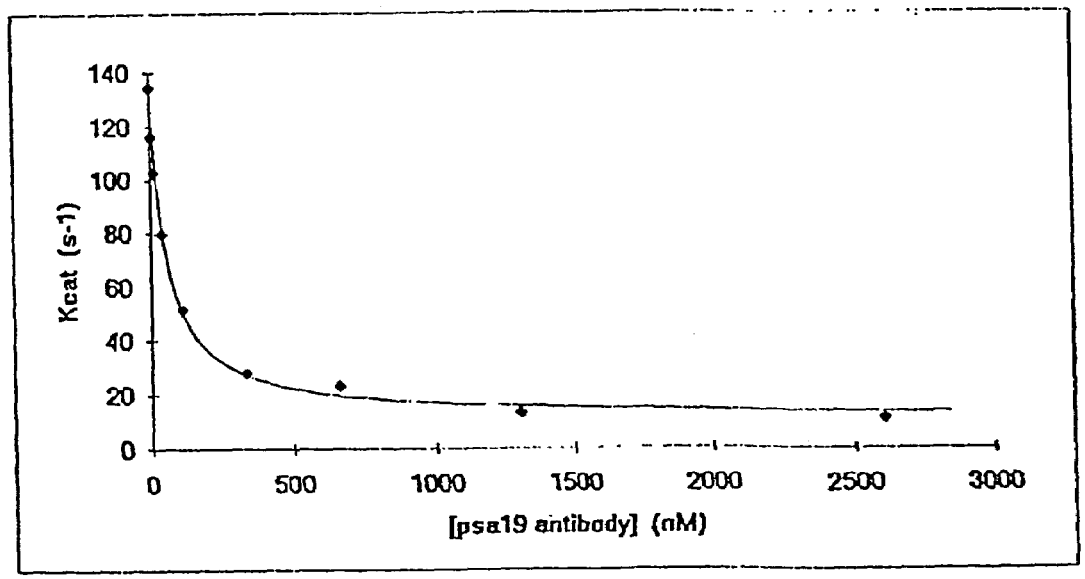
FIG. 4 is a curve showing the effect of psa19 antibody on the activity of chimeric p19Rb404.

Three rounds of selection were also applied to the rec4B library using the psa19 antibody. A clone was found whose activity was regulated by psa antibody binding (psa1919Rb404). The phage enzyme was diluted in 50 mM phosphate buffer at pH 7, at a concentration of $2.4 \times 10^{-9}$ M. The psa antibody was added at a final concentration which varies between zero and 2.6 µM. After 10 minutes, the substrate (benzyl-penicillin) was added at a final concentration of $5\times10^{-4}$ M. The activity was measured by determination of the rate of decrease of the decrease of the absorbance at 232 nm. A kcat of 134 $s^{-1}$ was found in absence of psa19. Psa19 binding inhibits the activity to 8% of that found in absence of antibody. Half of the effect is observed at a concentration of psa19 of 50 nM (Kd=$5\times10^{-8}$ M for the complex between psa19 and the β-lactamase mutant). See FIG. 4. The sequencing of this clone revealed that the wild type residues $E_{104}$–$Y_{105}$ were replaced by $Q_{104}$–$G_{105}$ and the wild type residue $T_{271}$ was replaced by the sequence GPW-PRQ. This sequence is not present in psa.

3. Summary.

Two large libraries have been constructed, i.e., lib3j and rec4b. These libraries are very active and permitted the selection on antibodies of clones whose kcat values range between 3 and 13% of that of the wild-type Fdbla clone. The construction of an active library was assumed to be a prerequisite in the finding of regulable β-lactamase mutants. Table 10 summarizes the results from screening lib3 and lib4.

A single successful affinity selection of the rec4b library has permitted clones that are strongly regulated by their binding partner, i.e., by the psa66 antibody.

insert. These clones arise from the in vivo selection for activity of the lib1 libraries because they have a growing advantage over the majority of the correctly but poorly active lib1 clones (clones containing incorrect inserts represent less than 0.1% of the non selected lib1 clones). In loop C, several 'extra' mutations are found outside the region mutagenised but inside the in vitro synthesized fragment used to clone the libraries. These clones seem also to have been preferentially amplified during the in vivo selection for activity. All the clones were tested on the penicillin substrate benzylpenicillin (PenG) and on the cephalosporin substrate PADAC. Only the results obtained with the substrate that gave the most important inhibitions are illustrated. Values of inhibition (relative activities) were determined in the presence of a saturating concentration of mAb.

Example 4

The lib1 library was analyzed by panning directly on the Dynabeads M280 to extract phage enzymes regulated by binding to streptavidin. A clone was found with a kcat of 20 $s^{-1}$, a binding constant of streptavidin Kd=$1.2\times10^{-7}$ and an inhibition factor of 1.3. Addition of biotin at a concentration of $5\times10^{-7}$ restored the activity to that observed in absence of

TABLE 10

Characteristics of the lib3 and lib4 clones selected on psa mAbs.

| selecting agent | clone | frq | sequence | substrate | Kcat (s–1) | relative activities (–/30 psa mAb) | kd (M) |
|---|---|---|---|---|---|---|---|
| | FdBla | — | wt | PenG | 1697 | 1/— | |
| | | | | PADAC | 666 | 1/— | |
| psa10 mAb | P10L4-01 | 9/11 | E104Y -> RN; T271 -> YSDDRV; R275 -> L | PenG | 320 | 1/0.18 | 7.5 10–7 |
| psa66 mAb | P661L3-01 | 4/5 | T271 -> TPGSLQ; R275 -> L | PADAC | 75 | 1/0.59 | 1.1 10–6 |
| | P66L4-01 | 3/12 | E104Y -> TG T271 -> DGSRIQ; R275 -> L | PADAC | 21 | 1/0.32 | 1.2 10–7 |
| | P66L4-03 | 2/12 | E104Y -> VG; T271 -> DGSRIQ; R275 -> L | PADAC | 30 | 1/0.34 | 1.9 10–7 |
| | P66L4-05 | 1/12 | V103E -> LLAG; T271 -> WLSPGF; R275 -> Q | PenG | 206 | 1/0.47 | 9.7 10–8 |
| | P66L4-06 | 1/12 | V103E -> LLAG; T271MDER -> DLGAV | PADAC | 637 | 1/0.38 | 3.6 10–7 |
| psa19 mAb | P19L3-01 | 2/6 | T271 -> SQPVKS; R275 -> Q | PenG | 245 | 1/0.19 | 5.2 10–9 |
| | P19L4-01 | 3/9 | E104Y -> QG; T271 -> GPQPRQ | PenG | 134 | 1/0.08 | 5.0 10–8 |
| | P19L4-04 | 1/9 | E104Y -> QG; T271 -> YFGPKL; R275 -> L | PenG | 321 | 1/0.24 | 2.7 10–7 |
| | P19L4-05 | 1/9 | E014Y -> QG; T271 -> PNTPEE; E274 -> K | PenG | 420 | 1/0.16 | 2.0 10–7 |

Characterization of several well-regulated clones isolated on psa mabs from the lib3 and lib4 libraries was performed. Most of the clones contain a complete insert in loop C (lib3 and lib4 clones) but only point mutations in loops A (lib4 clones). The lack of a complete insert in loop A results from the fact that about 50% of the active lib1 clones used for the construction of the lib4 library did not contain a complete streptavidin. The sequence of the peptide inserted between $L_{102}$ and $S_{106}$ in replacement of $V_{103}$–$Y_{105}$ was YHPQNS.

Example 5

Figure 5A:
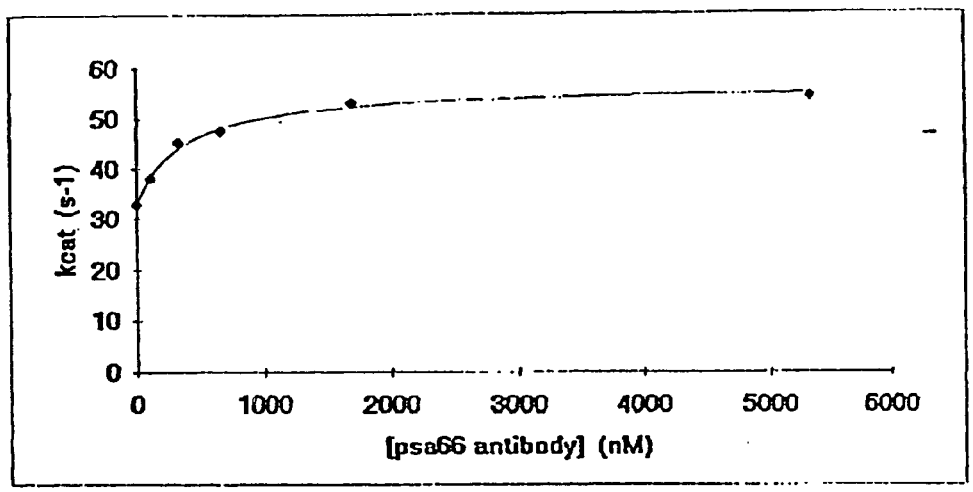
FIGS. 5A and 5B are curves showing the effect of psa66 antibody on the activity of chimeric p66Rb330 using two different substrates, Centa and PADAC, respectively.
Figure 5B:
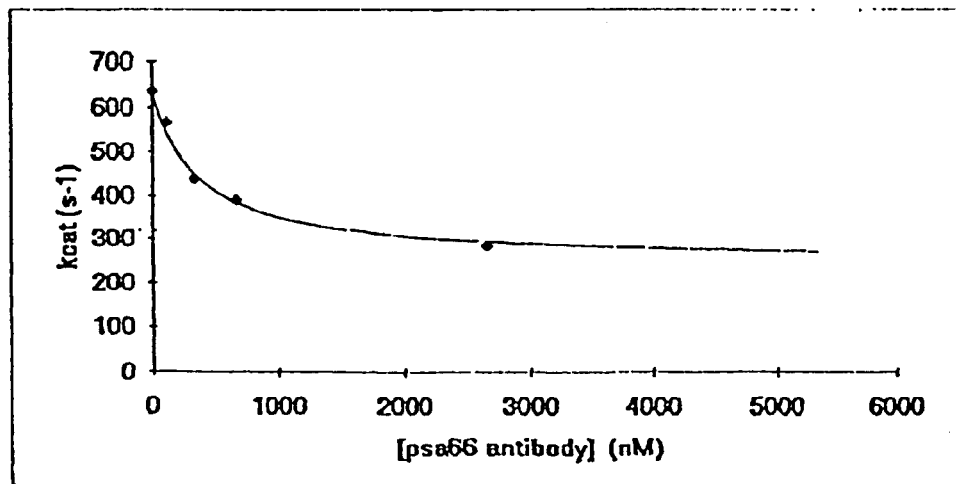
Figure 6:
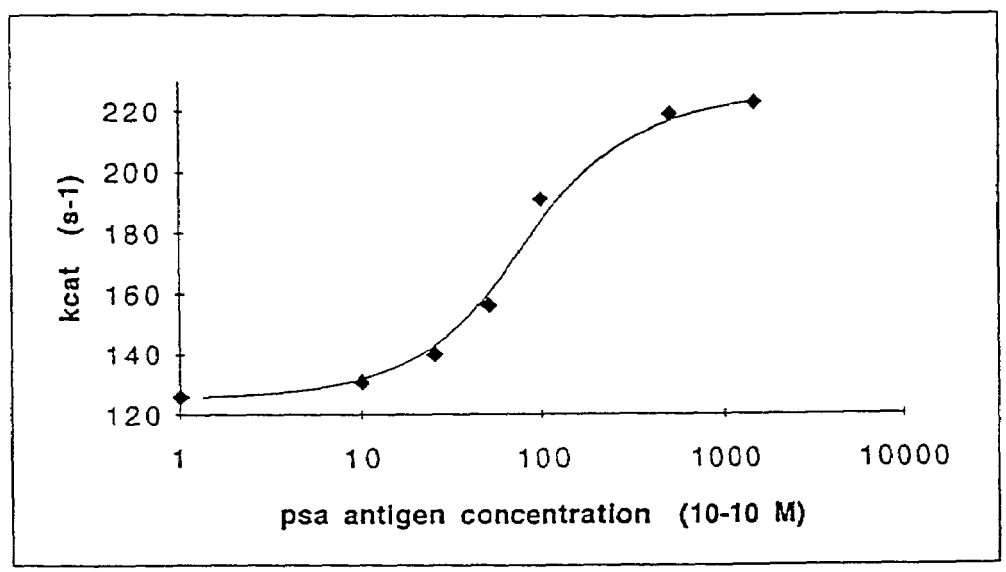
FIG. 6 is a curve showing an assay of psa antigen performed on PenG in the presence of phage-enzyme P19L3-01 and psa 19 mAb.

Three rounds of selection were carried out on the Rec4b library by panning using the psa66 antibody (CanAg diagnostics AB, Gothengburg, Sweden). Clone p66Rb330 was selected and analyzed for regulation of activity by psa66 binding. Two substrates were used. The effect observed depended on the substrate. See FIGS. 5A and 5B. With Centa as substrate, a 1.72 fold activation was observed. With PADAC, a 2.6 fold inhibition was observed. Both activation/inhibition curves can be fitted with the same binding constant between the monoclonal antibody psa66 and the enzyme Kd=360 nM. This clone has been sequenced: the wild type residues $V_{103}$–$Y_{105}$ were replaced by LLAGY and the wild type residues $T_{271}$–$R_{275}$ were replaced by DLGAV. These sequences are not present in PSA and thus the monoclonal antibody recognizes a mimotope.

Example 6

Library 3 was screened and clone P19L3-01 selected from it. See Example 3 and Table 10. This clone showed the best inhibition with the psa 19 mAb (kd=5 nM). This clone was grown up and used in a study of its response to competition with psa antigen and psa 10 mAb. PenG was used as a substrate in 50 mM phosphate buffer pH7.5, in the presence of 1 nM of the phage-enzyme P19L3-01, 5 nM of psa 19 mAb, 200 ng/ml of BSA with various concentrations of psa antigen. The levels of psa antigen were varied from 0.1 nM to 150 nM. The kcat ($s^{-1}$) was used as the measure of activity. See FIG. 8.

The entire disclosure of all applications, patents and publications, cited above and in the figures are hereby incorporated by reference.

It is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

What is claimed is:

1. A method for determining the presence or amount of an analyte in a test sample, comprising:
   forming a mixture of (1) a chimeric enzyme comprising β-lactamase and a binding site moiety, said binding site moiety including at least one amino acid, said chimeric enzyme having a sequence of said binding site moiety inserted in said enzyme or replacing at least one amino acid of said enzyme with the proviso that the activity of the chimeric enzyme is modulated upon binding of a binding molecule to the binding site moiety, (2) a test sample, (3) a binding molecule which binds to a binding site moiety of the chimeric enzyme and modulates the activity of the enzyme, and (4) a substrate upon which the chimeric enzyme catalytically acts; and
   detecting the amount of catalysis of the substrate and thereby determining the presence or absence of said analyte of interest.

2. The method of claim 1, wherein the analyte competes with the chimeric enzyme for binding to the binding molecule.

3. The method of claim 1, wherein the binding molecule is said analyte.

4. The method of claim 1, wherein the binding molecule is an antibody.

5. The method for determining the presence or amount of an analyte in a test sample, comprising:
   forming a mixture of (1) a chimeric enzyme comprising β-lactamase and a binding site moiety, said binding site moiety including at least one amino acid, wherein said chimeric enzyme having a sequence of said binding site moiety inserted in said enzyme or replacing at least one amino acid of said enzyme with the proviso that the activity of the chimeric enzyme is modulated upon binding of a binding molecule to the binding site moiety, (2) test sample, and (3) a substrate upon which the chimeric enzyme catalytically acts; and
   detecting the amount of catalysis of the substrate and thereby determining the presence or absence of said analyte of interest.

6. The method of claim 5, wherein the analyte is an antibody.

7. The method of claim 1, wherein the enzymatic activity of the chimeric enzyme in the unbound state is equivalent to that of the β-lactamase.

8. The method of claim 5, wherein the enzymatic activity of the chimeric enzyme in the unbound state is equivalent to that of the β-lactamase.

* * * * *